(12) United States Patent
Altmann

(10) Patent No.: US 7,825,141 B2
(45) Date of Patent: Nov. 2, 2010

(54) EPOTHILONE DERIVATIVES

(75) Inventor: Karl-Heinz Altmann, Reinach (CH)

(73) Assignee: Novartis AG, Basel (CH)

( * ) Notice: Subject to any disclaimer, the term of this patent is extended or adjusted under 35 U.S.C. 154(b) by 825 days.

(21) Appl. No.: 10/591,921

(22) PCT Filed: Mar. 15, 2005

(86) PCT No.: PCT/EP2005/002756

§ 371 (c)(1),
(2), (4) Date: May 30, 2007

(87) PCT Pub. No.: WO2005/090335

PCT Pub. Date: Sep. 29, 2005

(65) Prior Publication Data

US 2008/0114040 A1  May 15, 2008

(30) Foreign Application Priority Data

Mar. 16, 2004  (GB)  ................... 0405898.8

(51) Int. Cl.
*A61K 31/426* (2006.01)
*C07D 277/20* (2006.01)
(52) U.S. Cl. .......... 514/365; 548/203; 548/204
(58) Field of Classification Search ........ 548/203, 548/204; 514/365
See application file for complete search history.

(56) References Cited

U.S. PATENT DOCUMENTS

| | | | | |
|---|---|---|---|---|
| 6,288,237 B1 * | 9/2001 | Hoefle et al. | ............... | 548/203 |
| 6,380,394 B1 | 4/2002 | Nicolaou et al. | | |
| 6,441,186 B1 * | 8/2002 | Nicolaou et al. | ........... | 548/204 |
| 6,831,076 B2 * | 12/2004 | Hoefle et al. | ............... | 514/183 |
| 7,358,266 B2 * | 4/2008 | Nicolaou et al. | ........... | 514/370 |
| 2004/0039026 A1 | 2/2004 | Nicolaou et al. | | |

FOREIGN PATENT DOCUMENTS

| | | |
|---|---|---|
| WO | 97/19086 | 5/1997 |
| WO | WO 98/22481 A1 | 5/1998 |
| WO | 98/25929 | 6/1998 |
| WO | 99/28324 | 6/1999 |
| WO | 00/37473 | 6/2000 |
| WO | WO 00/50423 A1 | 8/2000 |
| WO | 03/018002 | 3/2003 |
| WO | 03/078411 | 9/2003 |
| WO | 2004/014919 | 2/2004 |

OTHER PUBLICATIONS

Nicolaou et al., "Designed epothilones: Combinatorial synthesis, tubulin assembly properties, and cytotoxic action against taxol, resistant tumor cells," Angewandte Chemie, International Edition, Verlag Chemie, Weinheim, DE, vol. 36(19), pp. 2097-2103 (1997).
Nicolaou et al., "Chemical synthesis and biological evaluation of novel epothilone B and trans-12, 13-cyclopropyl epothilone B analogues," Tetrahedron, vol. 58(32), pp. 6413-6432 (2002).
Altmann et al., "Synthesis and Biological Evaluation of Highly Potent Analogues of Epothilones B and D," Bioorganic and Medicinal Chemistry Letters 10(24):2765-2768 (2000).
Nicolaou et al., "Chemical Synthesis and Biological Evaluation of cis- and trans-12, 13-Cyclopropyl and 12, 13-Cyclobutyl Epothilones and Related Pyridine Side Chain Analogues," J. Am. Chem. Soc. 123(38):9313-9323 (2001).
Nicolaou et al., "The Olefin Metathesis Approach to Epothilone A and Its Analogues," J. Am. Chem. Soc. 119 (34):7960-7973 (1997).

* cited by examiner

*Primary Examiner*—Golam M Shameem

(57) ABSTRACT

Epothilone derivatives of Formula (I) and their use as a pharmaceutical.

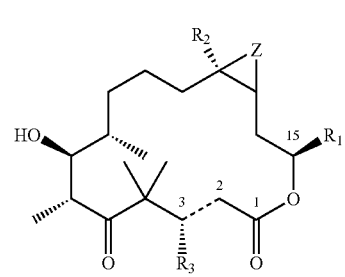

3 Claims, No Drawings

EPOTHILONE DERIVATIVES

The present invention relates to epothilone derivatives and their pharmaceutical use, pharmaceutical composition containing the same and methods for their preparation.

Despite the widespread use of Taxol® and Taxotere® in the treatment of many different tumor types, the impact of taxanes on patient survival has been modest, and the overwhelming majority of metastatic solid tumors remain incurable. Taxane treatment is associated with a number of significant side-effects, and the effectiveness of taxanes can be severely limited by the rapid development of drug resistance mechanisms. In view of these limitations as well as the side-effects commonly observed with standard combination therapies, there is a clear need for the identification of novel cytotoxic anti-cancer agents exhibiting an improved overall profile including spectrum of anti-tumor activity, efficacy against multi-drug resistant tumors, safety and tolerability.

The microtubule-stabilizing effect of the epothilones is first described by Bollag et al., Cancer Research 55, 1995, 2325-33. A suitable treatment schedule for the treatment of different types of tumors, especially tumors which are refractory to the treatment by other chemotherapeutics, in particular TAXOL™, using an epothilone, in particular epothilone A or B, is described in WO 99/43320. D. Su, A. Balog et al. discussed in Angew. Chem. Int. Ed. Engl. 1997, 36, pages 2093 to 2096, the structure-activity relationship of the class of the epothilones. On pages 2094 of said publication, they inter alia concluded that a modification of the structure of the natural compounds at the carbon atoms indicated as C1 to C8 results in a major loss of cytotoxicity and of loss of activity in the tubulin/microtubule system. Surprisingly, it has now been found that the C3-deoxy-epothilones of formula I have beneficial pharmacological properties and can be used for the treatment of proliferative diseases.

Hence, the present invention relates to epothilones of formula I

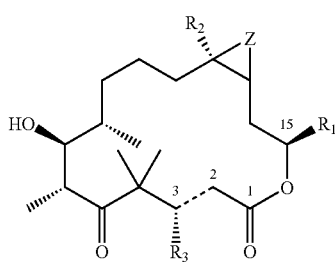

Wherein
$R_1$ is selected from

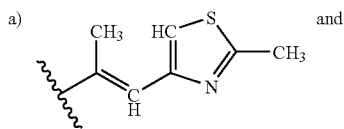

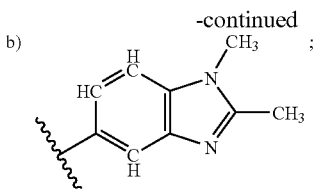

$R_2$ is lower alkyl or hydrogen
$R_3$ is OH or hydrogen;
Z is O, C or —Z— is a bond between the two binding carbon atoms;
⤳ is a single or double bond between C2 and C3;
or salts thereof;
with the proviso that when R1 is a, R3 is hydrogen and that when R1 is b, Z is O or a bond, and R2 is methyl R3 is not OH.

One embodiment of the invention is a compound of formula I
Wherein
$R_1$ is

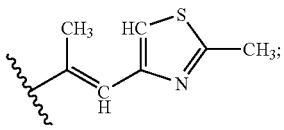

$R_2$ is lower alkyl preferably methyl
$R_3$ is hydrogen;
Z is O or —Z— is a bond between the two binding carbon atoms;
⤳ is a single bond;
or salts thereof.

A further embodiment of the invention is a compound of formula I
Wherein
$R_1$ is

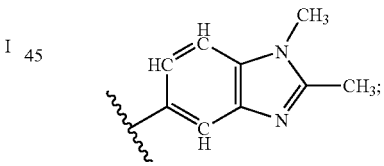

$R_2$ is lower alkyl or hydrogen
$R_3$ is OH or hydrogen;
Z is O, C or —Z— is a bond between the two binding carbon atoms;
⤳ is a single or double bond;
or salts thereof;
with the proviso that when R2 is methyl and Z is O or a bond R3 is not OH.

In a further embodiment the invention provides a compound selected from
(Z)-(7R,8S,9S,16S)-8-Hydroxy-5,5,7,9,13-pentamethyl-16-[(E)-1-methyl-2-(2-methyl-thiazol-4-yl)-vinyl]-oxacyclohexadec-13-ene-2,6-dione;
(1S,3S,10R,11S,12S,16R)-11-Hydroxy-8,8,10,12,16-pentamethyl-3-[(E)-1-methyl-2-(2-methyl-thiazol-4-yl)-vinyl]-4,17-dioxa-bicyclo[14.1.0]heptadecane-5,9-dione;

16-(1,2-Dimethyl-1H-benzoimidazol-5-yl)-8-hydroxy-5,5,
7,9-tetramethyl-oxacyclohexadec-13-ene-2,6-dione;
3-(1,2-Dimethyl-1H-benzoimidazol-5-yl)-11-hydroxy-8,8,
10,12-tetramethyl-4,17-dioxa-bicyclo[14.1.0]heptadecane-5,9-dione;
(Z)-(7R,8S,9S,16S)-16-(1,2-Dimethyl-1H-benzoimidazol-5-yl)-8-hydroxy-5,5,7,9,13-pentamethyl-oxacyclohexadec-13-ene-2,6-dione;
(1S,3S,10R,11S,12S,16R)-3-(1,2-Dimethyl-1H-benzoimidazol-5-yl)-11-hydroxy-8,8,10,12,16-pentamethyl-4,17-dioxa-bicyclo[14.1.0]heptadecane-5,9-dione;
(E)-(7R,8S,9S,16S)-16-(1,2-Dimethyl-1H-benzoimidazol-5-yl)-8-hydroxy-5,5,7,9-tetramethyl-oxacyclohexadec-13-ene-2,6-dione;
(1S,3S,10R,11S,12S,16S)-3-(1,2-Dimethyl-1H-benzoimidazol-5-yl)-11-hydroxy-8,8,10,12-tetramethyl-4,17-dioxa-bicyclo[14.1.0]heptadecane-5,9-dione;
16-(1,2-Dimethyl-1H-benzoimidazol-5-yl)-4,8-dihydroxy-5,5,7,9-tetramethyl-oxacyclohexadec-13-ene-2,6-dione;
3-(1,2-Dimethyl-1H-benzoimidazol-5-yl)-7,11-dihydroxy-8,8,10,12-tetramethyl-4,17-dioxa-bicyclo[14.1.0]heptadecane-5,9-dione;
(E)-(4S,7R,8S,9S,16S)-16-(1,2-Dimethyl-1H-benzoimidazol-5-yl)-4,8-dihydroxy-5,5,7,9-tetramethyl-oxacyclohexadec-13-ene-2,6-dione;
(1S,3S,7S,10R,11S,12S,16S)-3-(1,2-Dimethyl-1H-benzoimidazol-5-yl)-7,11-dihydroxy-8,8,10,12-tetramethyl-4,17-dioxa-bicyclo[14.1.0]heptadecane-5,9-dione;
(3E,13E)-(7R,8S,9S,16S)-16-(1,2-Dimethyl-1H-benzoimidazol-5-yl)-8-hydroxy-5,5,7,9-tetramethyl-oxacyclohexadeca-3,13-diene-2,6-dione;
(E)-(1S,3S,10R,11S,12S,16S)-3-(1,2-Dimethyl-1H-benzoimidazol-5-yl)-11-hydroxy-8,8,10,12-tetramethyl-4,17-dioxa-bicyclo[14.1.0]heptadec-6-ene-5,9-dione;
3-(1,2-Dimethyl-1H-benzoimidazol-5-yl)-7,11-dihydroxy-8,8,10,12-tetramethyl-4-oxa-bicyclo[14.1.0]heptadecane-5,9-dione; and
(1S,3S,7S,10R,11S,12S,16R)-3-(1,2-Dimethyl-1H-benzoimidazol-5-yl)-7,11-dihydroxy-8,8,10,12-tetramethyl-4-oxa-bicyclo[14.1.0]heptadecane-5,9-dione.

The prefix "lower" denotes a radical having up to and including a maximum of 7, especially up to and including a maximum of 4 carbon atoms, the radicals in question being either unbranched or branched with single or multiple branching.

Where the plural form is used for compounds, salts, and the like, this is taken to mean also a single compound, salt, or the like ("a" as an indefinite article or as a numeral meaning "one").

Asymmetric carbon atoms that are optionally present in the substituents may exist in the (R), (S) or (R,S) configuration, preferably in the (R) or (S) configuration. Substituents on a double bond or on a ring, for example on the carbon atoms to which Z in formula I is bonded, may be present in cis-(=Z—) or trans-(=E—) form. The present compounds may thus exist as mixtures of isomers or as pure isomers, preferably as pure diastereoisomers. Alkyl is preferably an alkyl radical with 1 to 10 carbon atoms, preferably lower alkyl, especially methyl.

Lower alkyl is unbranched or has mono- or multiple-branching and is in particular methyl or ethyl.

Salts are primarily the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, hydrohalic acids, such as hydrochloric acid, sulphuric acid, or phosphoric acid. Suitable organic acids are, for example, carboxylic, phosphonic, sulphonic or sulphamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, maleic acid, hydroxymaleic acid, methylmaleic acid, cyclohexanecarboxylic acid, benzoic acid, salicylic acid, 1- or 3-hydroxy-naphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, glucuronic acid, galacturonic acid, methane- or ethane-sulphonic acid, 2-hydroxyethanesulfonic acid, ethane-1,2-disulphonic acid, benzenesulphonic acid, 2-naphthalenesulphonic acid, 1,5-naphthalene-disulphonic acid, N-cyclohexylsulphamic acid, N-methyl-, N-ethyl- or N-propyl-sulphamic acid, or other organic protonic acids, such as ascorbic acid.

For isolation or purification purposes it is also possible to use pharmaceutically unacceptable salts, for example picrates or perchlorates. Only the pharmaceutically acceptable salts or free compounds (if the occasion arises, in the form of pharmaceutical preparations) attain therapeutic use, and these are therefore preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

The compounds of formula I have valuable pharmacological properties, as described hereinbefore and hereinafter.

The antiproliferative activity of the compounds of formula I may be proved as follows:

Stock solutions of the test compound of formula I 10 mM) in DMSO are prepared and stored at −20° C. Human KB-31 and (multidrug-resistant, P-gp 170 overexpressing) KB-8511 epidermoid carcinoma cells are from Dr. M. Baker, Roswell Park Memorial Institute (Buffalo, N.Y., USA) (for description see also Akiyama et al., Somat. Cell. Mol. Genetics 11, 117-126 (1985) und Fojo A., et al., Cancer Res. 45, 3002-3007 (1985)—KB-31 und KB-851 I both are derivatives of the KB-cell line (American Type Culture Collection) and are human epidermoid carcinoma cells. KB-31 cells can be cultivated in mono-layers using calf serum (M.A. Bio-products), L-glutamine (Flow), penicillin (50 Units/ml) und streptomycin (50 μg/ml (Flow); they then grow with a doubling rate of about 22 hours, and the relative efficiency of plating them out lies at about 60%. KB-8511 is a variant derived from the KB-31 cell line which has been obtained by treatment cycles with colchicine, and it shows an about 40-fold relative resistance against colchicin in comparison to KB-31 cells). The cells are incubated at 37° C. in an incubator with 5% V/V $CO_2$ and at 80% relative atmospheric humidity in MEM Alpha-medium which contains ribonucleosides und desoxyribonucleosides (Gibco BRL), complemented with 10 IU Penicillin, 10 μg/ml Streptomycin and 5% fetal calf serum. The cells are spread in an amount of $1.5 \times 10^3$ cells/well in 96-well-microtiter plates and incubated overnight. Serial dilutions of the test compounds in culture medium are added at day 1. The plates are then incubated for an additional period of four days, after which the cells are fixed using 3.3% v/v glutaraldehyde washed with water and finally stained with 0.05% w/v methylene blue. After washing again, the stain is eluted with 3% HCl and the optical density at 665 nm is measured with a SpectraMax 340 (Molecular Devices, Sunnyvale, Calif.). IC50-values are determined by mathematically fitting the data to curves using the SoftPro2.0 program (Molecular Devices, Sunnyvale, Calif.) and the formula

[(OD treated)−(OD start)]/[(OD control)−(OD start)]× 100.

The IC50 is defined as the concentration of a test compound at the end of the incubation period that leads to 50% of the number of cells in comparison to controls without test compound (concentration at halfmaximal inhibition of cell growth). Compounds of the formula I preferably show here and IC50 in the range from $0.1 \times 10^{-9}$ to $500 \times 10^{-9}$ M, preferably between 0.1 and 80 nM.

Owing to these properties, the compounds are suitable for the treatment of proliferative diseases, especially tumour diseases, including metastases; for example solid tumours such as lung tumours, breast tumours, colorectal tumours, prostate tumours, melanomas, brain tumours, pancreas tumours, neck tumours, bladder tumours, neuroblastomas, throat tumours, but also proliferative diseases of blood cells, such as leukaemia; also for the treatment of other diseases which respond to treatment with microtubule depolymerisation inhibitors, such as psoriasis.

In the following preparation processes for intermediates, functional groups which are to be in protected form can be protected if necessary at suitable stages, whereby selective protection or deprotection is also possible. The protecting groups and the methods of introducing and/or removing them correspond to those named above under process a), especially those named in the above-mentioned standard reference works or, in particular, in the examples. As a rule, protecting groups are not mentioned in the following; the following examples show where the usage of the protecting groups is appropriate or necessary and can therefore be regarded as a preferred instruction as to when protecting groups should be used and if compounds should be produced with other radicals. In the following, protecting groups are not mentioned at all the points where they are appropriately used. The person skilled in the art is clear as to where this usage ought to or must occur.

The compounds of formula I may be prepared by deprotection of a compound of formula II for example by treating with HF in an inert solvent such as acetonitrile.

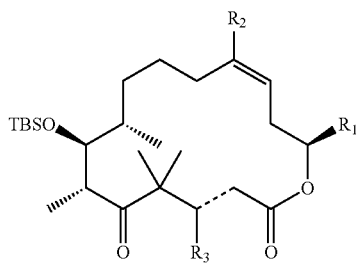

II

A compound of formula II may be prepared by ring closure of a compound of formula III

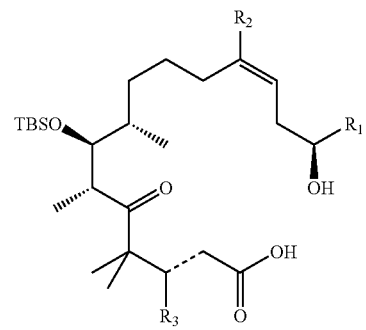

III

For example by first treating with trichlorobenzylchloride in the presence of a base such as triethylamine and then treating with DMAP preferably under dilute conditions.

A compound of formula III may be prepared by converting a compound of formula IV

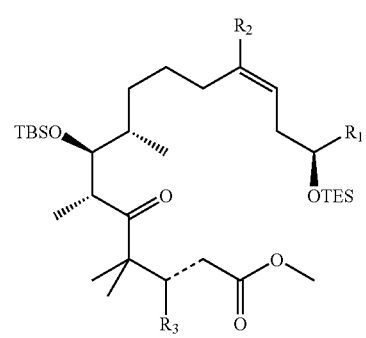

IV for example by treating with LiOH in a solvent such as i-PrOH/H$_2$O.

A compound of formula IV may be prepared by coupling a compound of formula V

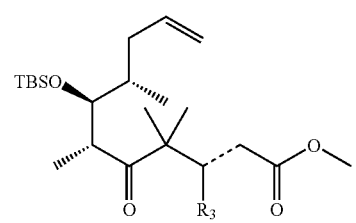

V

With a vinyl iodide of formula VI

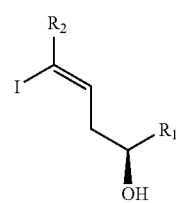

VI for example by first performing a hydroboration on a compound of formula V with a reagent such as 9-BBN then treating A vinyl iodide of formula VI with the resulting product in the presence of a catalyst such as Pd(dppf)$_2$Cl$_2$ and a reagent such as AsPh$_3$.

A compound of formula V may be prepared by treating a compound of formula VII

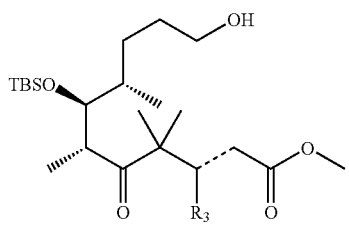

VII with NO2-PhSeCN, BU$_3$P followed by hydrogen peroxide and preferably a base.

A compound of formula VII may be prepared by hydrogenation of a compound of formula VIII

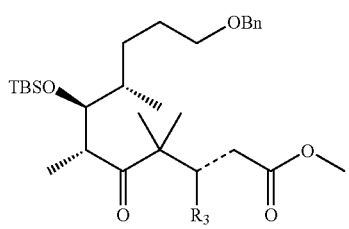

VIII for example using a palladium catalyst in the presence of hydrogen.

A compound of formula VIII may be prepared by first deprotonation of a compound of formula IX for example with LDA in the presence of a base preferably at a low temperature e.g. −78° C.

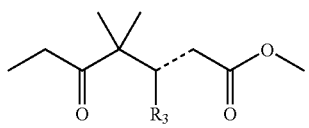

IX followed by treatment with an aldehyde of formula X

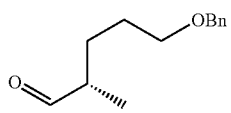

X

Compounds of formula I wherein Z is O may be prepared by first preparing the "13-ene" derivative and epoxidating for example by treating with methyltrioxorhenium in a solvent mixture of H$_2$O$_2$/H$_2$O/Pyridine.

Starting Materials

The starting materials are known, may be produced by known processes or are commercially available, or they may be produced as described in the following:

A compound of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I can besides or in addition be administered for tumour therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemopreventive therapy, for example in patients at risk.

Therapeutic agents for possible combination are especially one or more antiproliferative, cytostatic or cytotoxic compounds, for example one or more chemotherapeutic agent(s) selected from the group comprising the classical chemotherapeutic agents, an inhibitor of polyamine biosynthesis, an inhibitor of protein kinase, especially of serine/threonine protein kinase, such as protein kinase C, or of tyrosine protein kinase, such as epidermal growth factor receptor protein tyrosine kinase, a cytokine, a negative growth regulator, such as TGF-β or IFN-β, an aromatase inhibitor, and a classical cytostatic.

Compounds according to the invention are not only for the (prophylactic and preferably therapeutic) treatment of humans, but also for the treatment of other warm-blooded animals, for example of commercially useful animals, for example rodents, such as mice, rabbits or rats, or guinea-pigs. They may also be used as a reference standard in the test systems described above to permit a comparison with other compounds.

A compound of formula I may also be used for diagnostic purposes, for example with tumours that have been obtained from warm-blooded animal "hosts", especially humans, and implanted into mice to test them for decreases in growth after treatment with such a compound, in order to investigate their sensitivity to the said compound and thus to improve the detection and determination of possible therapeutic methods for neoplastic diseases in the original host.

Within the groups of preferred compounds of formula I mentioned hereinafter, definitions of substituents from the general definitions mentioned hereinbefore may reasonably be used, for example, to replace more general definitions with more specific definitions or especially with definitions characterized as being preferred; the definitions characterised as being preferred, or exemplary ("e.g.", "such as", "for example"), are preferred.

The following examples illustrate the invention, but are not intended to restrict their scope in any way.

Temperatures are measured in degrees celsius. Unless otherwise indicated, the reactions take place at room temperature.

| Table of abreviations | |
|---|---|
| HF | Hydrofluoric acid |
| 9-BBN | 9-borabicyclo-nonane |
| AcOEt | Ethyl acetate |
| AcOH | Acetic acid |
| AsPh$_3$ | Triphenylarsine |
| Bu$_3$P | Tributyl phosphine |
| Bu$_4$N(HSO$_4$) | Tetrabutylammonium hydrogen sulfate |
| BuLi | Butyl lithium |
| CH$_2$Cl$_2$ | Dichloromethane |
| CH$_2$I$_2$ | Methylene iodide |
| CH$_3$CN | Acetonitrile |
| CHI$_3$ | Iodoform |

Table of abreviations

| | |
|---|---|
| CrCl$_2$ | Chromium chloride |
| CrCl$_2$ | Chrome chloride |
| CSA | (+)-Camphor-10-sulfonic acid |
| CsCO$_3$ | Cesium carbonate |
| DIAD | Diisopropyl-azodicarboxylate |
| DMAP | Dimethylaminopyridine |
| DMF | Dimethylformamide |
| DMM | Dimethoxymethane |
| Et$_2$O | Diethyl ether |
| Et$_2$Zn | Diethyl zinc |
| H$_2$O | water |
| H$_2$O$_2$ | Hydrogen peroxide |
| Hex | Hexane |
| i-Pr$_2$NH | Diisopropyl amine |
| i-PrOH | isopropanol |
| K$_2$CO$_3$ | Potassium carbonate |
| KHSO$_4$ | Potassium hydrogenosulfate |
| LiOH | Lithium hydroxide |
| MeOH | Methanol |
| MgSO$_4$ | Magnesium sulfate |
| MTO | Methyltrioxorhenium |
| Na$_2$B$_4$O$_7$.10 H$_2$O | Sodium tetraborat-decahydrat |
| Na$_2$EDTA | Ethylenediaminetetraacetic acid disodium salt |
| Na$_2$SO$_4$ | Sodium sulfate |
| NaHCO$_3$ | Sodium bicarbonate |
| NH$_4$Cl | Ammonium chloride |
| Pd(dppf)$_2$Cl$_2$ | 1,1-Bis(diphenylphosphino) ferrocene palladium chloride |
| Pd/C | Palladium on charcoal |
| Ph$_3$P | triphenylphosphine |
| Rf | Retention to front |
| TBAF | Tetra butylammonium fluoride |
| TBSOTf | f-Butyldimethylsilyl trifluoromethanesulfonate |
| TESCl | Triethylsilyl chloride |
| TESOTf | Triethylsilyl trifluorornethanesulfonate |
| TFA | Trifluoroacetic acid |
| THF | Tetrahydrofuran |
| TLC | Thin layer chromatography |

EXPERIMENTAL PART

Example 1

(Z)-(7R,8S,9S,16S)-8-Hydroxy-5,5,7,9,13-pentamethyl-16-[(E)-1-methyl-2-(2-methyl-thiazol-4-yl)-vinyl]-oxacyclohexadec-13-ene-2,6-dione (14)

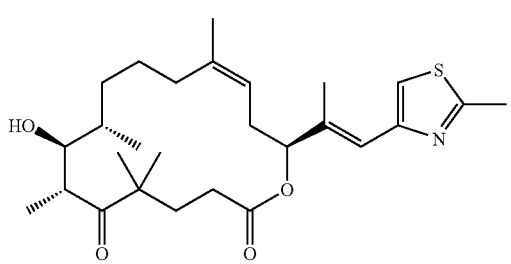

To a solution of 13 (50 mg, 0.085 mmol) in 3 mL CH$_3$CN and in a Teflon tube is added at rt 0.6 mL of HF.Pyridine (70/30) and the reaction mixture is stirred for 2 h at rt. The reaction mixture is washed with a 5% solution of NaHCO$_3$, extracted 3 times with 10 mL AcOEt and then the organic layers are dried (MgSO$_4$). Purification by flash column chromatography (Hexane/Et$_2$O—90/10 to 50/50) afforded 14 as a colourless oil.

ESI-MS: M(C$_{27}$H$_{41}$NO$_4$S)=475.7, (M+H)$^+$=476.1.

Rf: Hexane/Acetone—50/50: 0.61.

$^1$H NMR (400 MHz, CDCl$_3$): δ=7.00 (s, 1H, NC=CHS), 6.60 (s, 1H), 5.25 (m, 1H), 5.15 (m, 1H), 3.70 (m, 1H), 3.20 (m, 1H), 2.90 (s, 3H), 2.60 (m, 2H), 2.30 (m, 2H), 2.10 (m, 2H), 2.05 (s, 3H), 1.95 (m, 1H), 1.60 (s, 3H), 1.30 (s, 6H), 1.20 (d, 3H), 1.00 (d, 3H).

(1a)—Compound 2

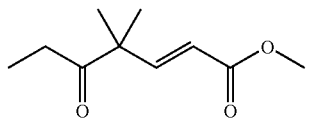

To a solution of Phosphonoacetate (10.2 g, 0.048 mmol) in 50 mL THF, under argon at 0° C., isadded dropwise a 1.6M solution of n-BuLi (30.5 mL, 0.048 mmol) and the reaction mixture isstirred at 0° C. over 30 min. The solution iscooled to −78° C. and aldehyde 1 (5 g, 0.039 mmol) in 10 mL THF isadded dropwise in 10 min. The reaction mixture isstirred at rt for 2 h and quenched with a saturated solution of NH$_4$Cl, extracted 3 times with 20 mL Et$_2$O. The combined organic layers are dried (MgSO$_4$) and concentrated in vacuum. Purification by flash column chromatography (Hexane/Et$_2$O—90/10) afforded 2 as an oil.

ESI-MS: M(C$_{10}$H$_{16}$O$_3$)=184.2, (M+H$_2$O)$^+$=202.0.

Rf: Hexane/Acetone—50/50: 0.68.

$^1$H NMR (400 MHz, CDCl$_3$): δ=7.00 (d, 1H), 5.85 (d, 1H), 3.75 (s, 3H), 2.45 (q, 2H), 1.25 (s, 6H), 1.00 (t, 3H).

(1b)—Compound 4

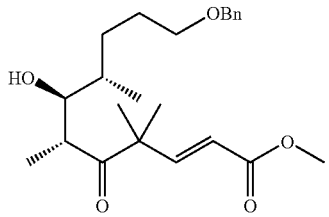

To a solution of i-Pr$_2$NH (0.135 mL, 0.969 mmol) in 2.5 mL THF at 0° C. is added dropwise over 10 min a 1.6M solution of n-BuLi (0.6 mL, 0.969 mmol). The mixture is stirred at 0° C. for 30 min and then is cooled to −78° C. for addition dropwise over 20 min of 2 (0.18 g, 0.969 mmol) in 2 mL THF. After 1 h, aldehyde 3 is added (0.1 g, 0.484 mmol) in 2 mL THF and the reaction mixture is stirred for another 1 h at −78° C. and then is quenched with a saturated solution of NH$_4$Cl, extracted 3 times with 10 mL CH$_2$Cl$_2$. The combined organic layers are dried (MgSO$_4$) and concentrated in vacuum. Purification by flash column chromatography (Hexane/Acetone—90/10) afforded 4 in a 2.5/1 ratio.

Rf: Hexane/Acetone—50/50: 0.70.

$^1$H NMR (400 MHz, CDCl$_3$): δ=7.30 (m, 5H), 7.00 (d, 1H), 5.95 (d, 1H), 4.50 (s, 2H), 3.75 (s, 3H), 3.45 (m, 2H), 3.35 (m, 1H), 3.15 (m, 1H), 1.75 (m, 2H), 1.55 (m, 2H), 1.30 (s, 6H), 1.05 (d, 3H), 0.80 (d, 3H).

ESI-MS: M(C$_{23}$H$_{34}$O$_5$)=390.5, (M+H)$^+$=391.2.

(1c)—Compound 5

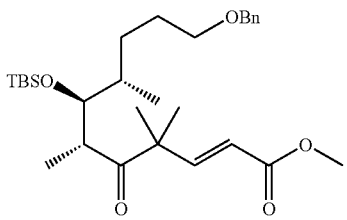

To a solution of 4 (0.4 g, 1.024 mmol) in 5 mL CH$_2$Cl$_2$ at 0° C. is added dropwise 2,6-lutidine (0.24 mL, 2.048 mmol) followed by TBSOTf (0.35 mL, 1.536 mmol). The mixture is stirred at 0° C. for 2 h and then is quenched with a saturated solution of NH$_4$Cl, extracted 3 times with 25 mL CH$_2$Cl$_2$. The combined organic layers are dried (MgSO$_4$) and concentrated in vacuum. Purification by flash column chromatography (Hexane/Et$_2$O—90/10) afforded 5 as an oil.

ESI-MS: M(C$_{29}$H$_{48}$O$_5$Si)=504.8, (M+H$_2$O)$^+$=522.1.

Rf: Hexane/Acetone—50/50: 0.80.

$^1$H NMR (400 MHz, CDCl$_3$): δ=7.30 (m, 5H), 7.10 (d, 1H), 5.90 (d, 1H), 4.50 (s, 2H), 3.82 (m, 1H), 3.75 (s, 3H), 3.40 (m, 2H), 3.05 (m, 1H), 1.70 (m, 2H), 1.40 (m, 2H), 1.30 (2s, 6H), 1.05 (d, 3H), 0.92 (d, 3H) 0.89 (s, 9H), 0.05 (s, 6H).

(1d)—Compound 6

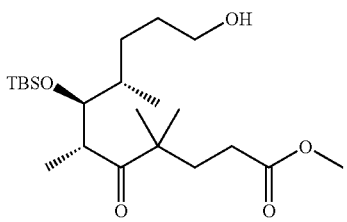

To a solution of 5 (0.45 g, 0.89 mmol) in 10 mL MeOH at rt is added Pd/C (0.1 g, 10%) and the reaction mixture is stirred under a 5 bar pressure of H$_2$ for 6 h. The mixture is filtered on hyflo and purification by flash column chromatography (Hexane/Et$_2$O—80/20 to 50/50) afforded 6 as a colourless oil.

ESI-MS: M(C$_{22}$H$_{44}$O$_5$Si)=416.7, (M+H)$^+$=417.2.

Rf: Hexane/Acetone—50/50: 0.70.

$^1$H NMR (400 MHz, CDCl$_3$): δ=3.80 (m, 1H), 3.75 (s, 3H), 3.60 (m, 2H), 3.15 (m, 1H), 2.20 (m, 2H), 1.80 (m, 2H), 1.40-1.70 (m, 4H), 1.15 (2s, 6H), 1.05 (d, 3H), 0.92 (d, 3H) 0.89 (s, 9H), 0.05 (s, 6H).

(1e)—Compound 7

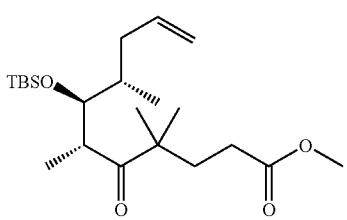

To a solution of 6 (0.35 g, 0.84 mmol) in 10 mL THF at rt is added NO$_2$-PhSeCN (1.16 g, 4.2 mmol) followed by Bu$_3$P (1 mL, 4.2 mmol). The reaction mixture is stirred at rt for 2 h before the addition of NaHCO$_3$ (2.11 g, 25.2 mmol) and a 30% solution of H$_2$O$_2$ (2.6 mL, 25.2 mmol). The solution is stirred for 2 h at rt and then is quenched with a saturated solution of NH$_4$Cl, extracted 3 times with 10 mL CH$_2$Cl$_2$. The combined organic layers are dried (MgSO$_4$) and concentrated in vacuum. Purification by flash column chromatography (CH$_2$Cl$_2$—100 then Hexane/Et$_2$O—90/10 to 50/50) afforded 7 as colourless oil.

ESI-MS: M(C$_{22}$H$_{42}$O$_4$Si)=398.7, (M+H)$^+$=399.2.

Rf: Hexane/Acetone—70/30: 0.61.

$^1$H NMR (400 MHz, CDCl$_3$): δ=5.70 (m, 1H), 5.00 (m, 2H), 3.80 (m, 1H), 3.75 (s, 3H), 3.20 (m, 1H), 2.20 (m, 2H), 1.85 (m, 2H), 1.40 (m, 2H), 1.20 (s, 3H), 1.15 (s, 3H), 1.05 (d, 3H), 0.92 (d, 3H), 0.89 (s, 9H), 0.05 (s, 6H).

(1f)—Compound 11

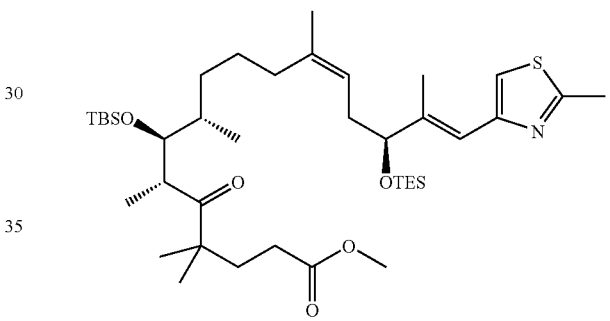

To a 0.5M solution of 9-BBN in 2 mL THF (2.3 mL, 1.154 mmol) is added dropwise 7 (0.23 g, 0.577 mmol) in 2 mL THF at rt. After 2 h TLC analysis revealed the complete consumption of the starting olefin. In a separate flask, containing vinyl iodide 10 (0.27 g, 0.577 mmol) in 2 mL DMF were added successively, CsCO$_3$ (0.37 g, 1.15 mmol), AsPh$_3$ (35 mg, 0.115 mmol), Pd(dppf)$_2$Cl$_2$ (85 mg, 0.115 mmol) and H$_2$O (0.31 mL, 17.3 mmol). In first solution is added H$_2$O (0.11 mL, 5.8 mmol) to quench the excess 9-BBN and the alkyl borane solution is added rapidly by syringe to the solution containing the vinyl iodide. The reaction mixture is stirred at rt overnight and quenched with H$_2$O, extracted 3 times with 20 mL Et$_2$O. The combined organic layers are dried (MgSO$_4$) and concentrated in vacuum. Purification by flash column chromatography (Hexane/Et$_2$O—90/10 to 50/50) afforded 11 as a colourless oil.

ESI-MS: M(C$_{40}$H$_{73}$NO$_5$Si$_2$S)=736.3, (M+H)$^+$=737.1.

Rf: Hexane/Acetone—70/30: 0.58.

$^1$H NMR (400 MHz, CDCl$_3$): δ=6.90 (s, 1H), 6.45 (s, 1H), 5.10 (m, 1H), 4.07 (t, 1H), 3.80 (m, 1H), 3.75 (s, 3H), 3.10 (m, 1H), 2.70 (s, 3H), 2.40 (m, 2H), 2.20 (m, 2H, CH$_2$CH$_2$CO$_2$Me), 1.99 (s, 3H), 1.90 (m, 2H), 1.65 (s, 3H), 1.50 (m, 2H), 1.20 (s, 3H), 1.10 (s, 3H), 1.05 (d, 3H), 0.95 (d, 3H), 0.92 (t, 9H), 0.89 (s, 9H), 0.57 (q, 6H), 0.05 (s, 6H).

(1g)—Compound 12

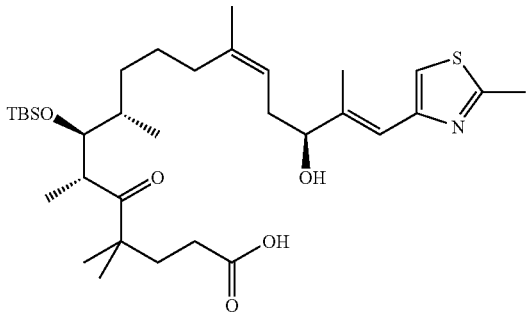

To a solution of 11 (0.22 g, 0.3 mmol) in 9 mL i-PrOH/H$_2$O—4/1 is added LiOH (43 mg, 1.8 mmol) and the mixture is heated at 60° C. and stirred overnight. After cooling to rt, the solution is quenched with a saturated solution of NH$_4$Cl, extracted twice with 10 mL CH$_2$Cl$_2$ and twice with 10 mL AcOEt. The combined organic layers are dried (MgSO$_4$) and concentrated in vacuum. The crude reaction mixture is used directly in the next step.

ESI-MS: M(C$_{33}$H$_{57}$NO$_5$SiS)=607.9, (M+H)$^+$=608.1.
Rf: Hexane/Acetone—70/30: 0.25.
$^1$H NMR (400 MHz, CDCl$_3$): δ=6.90 (s, 1H), 6.45 (s, 1H), 5.15 (m, 1H), 4.07 (q, 1H), 3.80 (m, 1H), 3.20 (m, 1H), 2.70 (s, 3H), 2.30 (m, 2H), 2.10 (m, 2H), 1.99 (s, 3H), 1.90 (m, 2H), 1.70 (s, 3H), 1.40 (m, 2H), 1.20 (s, 3H), 1.10 (s, 3H), 1.05 (d, 3H), 0.95 (d, 3H), 0.89 (s, 9H), 0.05 (s, 3H), 0.03 (s, 3H).

(1h)—Compound 13: (Z)-(7R,8S,9S,16S)-8-(tert-Butyl-dimethyl-silanyloxy)-5,5,7,9,13-pentamethyl-16-[(E)-1-methyl-2-(2-methyl-thiazol-4-yl)-vinyl]-oxacyclohexadec-13-ene-2,6-dione

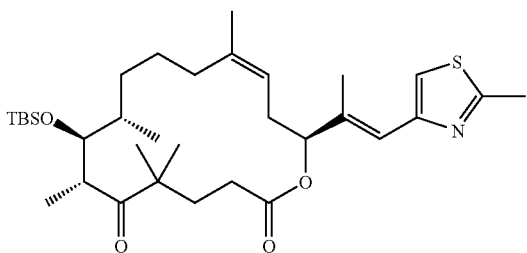

To a solution of 12 (190 mg, 0.312 mmol) in 8 mL THF at 0° C. is added triethylamine (0.26 mL, 1.87 mmol) followed by trichlorobenzylchloride (0.24 mL, 1.56 mmol). After stirring for 20 min at rt, the solution is diluted with 15 mL dry toluene and the resulting solution is added slowly in 2 h to a previously prepared solution of DMAP (0.38 mg, 3.12 mmol) in 200 mL toluene. The reaction mixture is stirred at rt for 30 min and then concentrated in vacuum. The crude product is purified by flash column chromatography (Hexane/Et$_2$O—70/30) to afford 13 as an oil.

ESI-MS: M(C$_{33}$H$_{55}$NO$_4$SiS)=589.9, (M+H)$^+$=590.1.
Rf: Hexane/Acetone—50/50: 0.74.
$^1$H NMR (400 MHz, CDCl$_3$) for major compound: δ=6.90 (s, 1H), 6.45 (s, 1H), 5.25 (m, 1H), 5.10 (m, 1H), 3.80 (m, 1H), 3.10 (m, 1H), 2.70 (s, 3H), 2.30 (m, 2H), 2.10 (m, 2H), 2.05 (s, 3H), 1.80 (m, 2H, CH$_2$CH$_2$CO$_2$), 1.60 (s, 3H), 1.30 (m, 2H), 1.20 (s, 6H), 1.10 (d, 3H), 1.00 (d, 3H), 0.89 (s, 9H), 0.05 (s, 3H), 0.01 (s, 3H).

Example 2

(1S,3S,10R,11S,12S,16R)-11-Hydroxy-8,8,10,12,16-pentamethyl-3-[(E)-1-methyl-2-(2-methyl-thiazol-4-yl)-vinyl]-4,17-dioxa-bicyclo[14.1.0]heptadecane-5,9-dione (15)

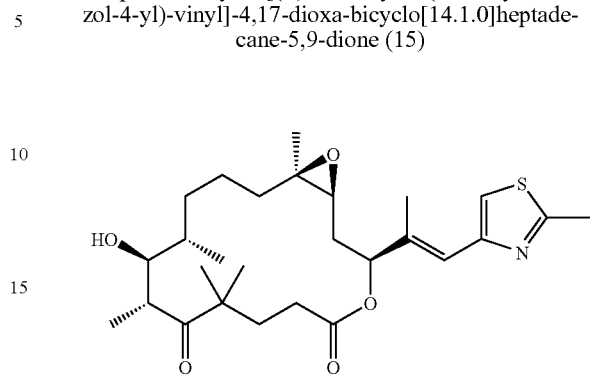

To a solution of 14 (8 mg, 0.017 mmol) in 0.8 mL of CH$_2$Cl$_2$ at rt is added a 300 μL of a solution H$_2$O$_2$/H$_2$O/Pyridine—16/140/1 and MTO (2 mg, 0.0084 mmole). The reaction mixture is stirred at rt for 1 h30 and then is quenched with a saturated solution of NH$_4$Cl and extracted twice with 10 mL CH$_2$Cl$_2$. The combined organic layers are dried (MgSO$_4$) and concentrated in vacuum. Purification by flash column chromatography (Hexane/Acetone—90/10 to 70/30) afforded 15 in a 9/1 ratio in favour of desired epoxide.

ESI-MS: M(C$_{27}$H$_{41}$NO$_4$S)=491.7, (M+H)$^+$=492.2.
Rf: Hexane/Acetone—50/50: 0.52.
$^1$H NMR (400 MHz, CD$_3$OD): δ=7.20 (s, 1H, NC=CHS), 6.80 (s, 1H), 5.40 (m, 1H), 3.60 (m, 1H), 3.20 (m, 1H), 2.95 (m, 1H, CH—O), 2.70 (s, 3H, CH$_3$CN), 2.40 (m, 2H, CH$_2$CH—O), 2.20 (m, 2H), 2.05 (s, 3H), 1.95 (m, 2H), 1.60 (s, 3H), 1.30 (s, 6H), 1.20 (d, 3H), 1.00 (d, 3H).

Example 3

16-(1,2-Dimethyl-1H-benzoimidazol-5-yl)-8-hydroxy-5,5,7,9-tetramethyl-oxacyclohexadec-13-ene-2,6-dione (Compound 22)

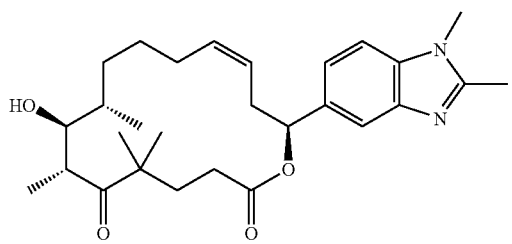

To a 50 ml plastic tube, equipped with a magnetic stir bar, are successively added 21 (339 mg), 20 ml of acetonitrile and 20 ml of tetrahydrofuran. To this solution is rapidly added HF-Pyridine complex (7 ml). The reaction is monitored by TLC (CH$_2$Cl$_2$/MeOH: 95/5) and the mixture is stirred at room temperature for 3 h. The reaction mixture is then carefully added dropwise to an Erlenmeyer containing CH$_2$Cl$_2$ (100 ml), distilled water (100 ml) and sodium bicarbonate (30 g). The two layers are separated by decantation and the aqueous phase is extracted three times with CH$_2$Cl$_2$ (100 ml). After drying with magnesium sulfate, the solvents are removed under vacuo and the crude mixture is purified by flash chromatography (CH$_2$Cl$_2$/MeOH: 98/2 to 97/3) to finally give 22 as a white solid.

ESI-MS: 468.9 (M+H)$^+$.
HPLC: Rt=7.58 min.
Rf=0.54 (Hex/acetone: 30/70).
$^1$H-NMR (400 MHz, CDCl$_3$/ppm): 7.71 (s, 1H), 7.27 (m, 2H), 6.00 (dd, 3.7 Hz, 1H), 5.48 (m, 2H), 3.76 (s, 3H), 3.74 (m, 1H), 3.19 (qd, 3.7 Hz, 1H), 2.97-2.84 (m, 2H), 2.64 (s, 3H), 2.45-2.01 (m, 6H), 1.81-1.64 (m, 4H), 1.49-1.16 (m, 3H), 1.30 (s, 3H), 1.21 (d, 7 Hz, 3H), 1.06 (d, 7 Hz, 3H), 1.02 (s, 3H).

(3a)—Compound 17

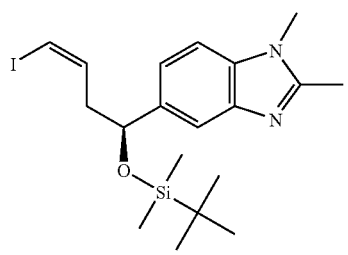

Sodium bis(trimethylsilyl) amide (18.0 ml of a 1M THF solution) is slowly added at room temperature to a suspension of the finely crushed iodomethyl-triphenylphosphonium iodide (9.9 g) in 50 ml THF. The solution becomes quickly orange. After the end of the addition (~15 min), the mixture is cooled down to –78° C. and the aldehyde 16 (4.98 g) in THF (20 ml) is added drop wise. After 30 min stirring at –78° C., the reaction is quenched by the addition of a saturated solution of ammonium chloride (50 ml) under vigorous stirring. The mixture is then allowed to warm up to room temperature and CH$_2$Cl$_2$ is added (100 ml). The two layers are separated by decantation and the aqueous phase is extracted twice with CH$_2$Cl$_2$ (50 ml). After drying of the joined organic phases with sodium sulfate and evaporation of the solvents under vacuo, the residue is taken in hexane (50 ml) in order to precipitate the triphenylphosphine oxide. The precipitate is filtered off and washed with hexane (5 ml) and the solvent of the filtrate is removed under vacuo. This procedure is repeated twice until no more phosphine oxide is present in hexane solution (controlled by TLC). The crude is then purified by Flash chromatography (Hexane/acetone: 90/10 to 60/40) to yield 17, as a clear oil which solidifies within two weeks at 4° C.
ESI-MS: 456.9 (M+H)$^+$.
Rf=0.54 (CH$_2$Cl$_2$/MeOH: 90/10).
$^1$H-NMR (400 MHz, CDCl$_3$/ppm): 7.63 (bs, 1H), 7.23 (m, 2H), 6.22 (m, 2H), 4.90 (false triplet, 1H), 3.72 (s, 3H), 2.65-2.46 (m, 2H), 2.61 (s, 3H), 0.88 (s, 9H), 0.04 (s, 3H), –0.14 (s, 3H).

(3b)—Compound 18

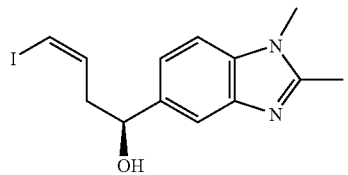

Camphorsulfonic acid (6.5 g, 28 mmol) is added carefully (~10 installments) in a solution of 17 (3.19 g, 7 mmol) in methylene chloride (150 ml) and methanol (150 ml) at 0° C. The mixture is then allowed to warm up to room temperature and is stirred for 17 h. The mixture is then carefully poured in an Erlenmeyer containing distilled water (500 ml) and sodium bicarbonate (4.7 g) under vigorous stirring. The layers are separated and the aqueous phase is extracted three times with CH$_2$Cl$_2$ (150 ml). The organic phases are joined, dried over sodium sulfate and the solvents are removed under vacuo. The crude, a yellow solid (2.4 g) is purified by three successive recrystallization (Hexane/CH$_2$Cl$_2$/MeOH: 50/50/1) in order to give 18, a slight yellow solid.
ESI-MS: 343.0 (M+H)$^+$.
Rf=0.35 (CH$_2$Cl$_2$/MeOH: 90/10).
$^1$H-NMR (400 MHz, CDCl$_3$/ppm): 7.66 (s, 1H), 7.29 (m, 2H), 6.29 (m, 2H), 4.97 (m, 1H), 3.75 (s, 3H), 2.78-2.62 (m, 2H), 2.62 (s, 3H).

(3c)—Compound 19

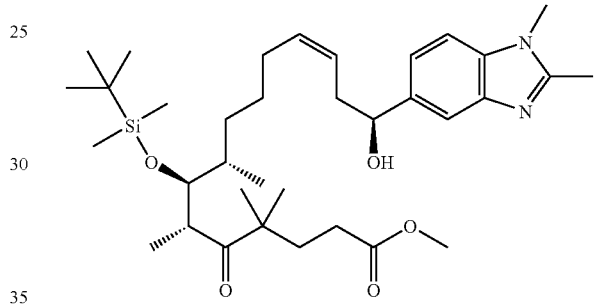

Flask A: To a solution of 7 (1.0 g) in 15 ml THF is added 9-BBN (10 ml of a 0.5M solution in THF) drop wise at 0° C. After the end of the addition, the ice bath is removed and the reaction mixture is allowed to warm up to room temperature. The reaction is monitored by TLC and is complete after 100 minutes. The excess of 9-BBN is quenched by addition of 200 µl of distilled water.

Flask B: In a 100 ml three-necked round bottomed flask, are successively added the vinyl iodide TI-35 (684 mg) and 25 ml of DMF. The solution is cooled down to 0° C. and Cesium carbonate (1.36 g), Triphenylarsine (122 mg), the Palladium catalyst (340 mg) and distilled water (1 ml) are successively added. The content of Flask A is then rapidly added (30 sec) under vigorous stirring. After 10 minutes at 0° C., the ice bath is removed and the reaction mixture is allowed to warm up to room temperature. The reaction is monitored by MS and is complete after 1 h15. The mixture is then poured in a 1 L Erlenmeyer containing 300 ml of diethyl ether and 300 ml of distilled water. The two layers are separated by decantation and the aqueous phase is extracted twice with 200 ml of diethyl ether. The organic phases are joined and dried with magnesium sulfate. Evaporation of the solvents under vacuo yielded a brown oil (4.0 g) which is purified by flash chromatography (Hexanes/Acetone: 70/30 to 30/70) to finally yield 19 as a thick yellow oil.
ESI-MS: 615.2 (M+H)$^+$.
Rf=0.24 (Hex/acetone: 50/50).
$^1$H-NMR (400 MHz, CDCl$_3$/ppm): 7.58 (s, 1H), 7.21 (m, 2H), 5.50-5.27 (m, 2H), 4.76 (dd, 1H), 3.74 (dd, 1H), 3.66 (s, 3H), 3.59 (s, 3H), 3.08 (m, 1H), 2.63-2.31 (m, 2H), 2.54 (s, 3H), 2.16 (m, 2H), 1.96 (m, 2H), 1.77 (m, 4H), 1.34-0.94 (m, 3H), 1.11 (s, 3H), 1.05 (s, 3H), 0.98 (d, 3H), 0.84 (s, 9H), 0.81 (d, 3H), 0.01 (s, 6H).

(3d)—Compound 20

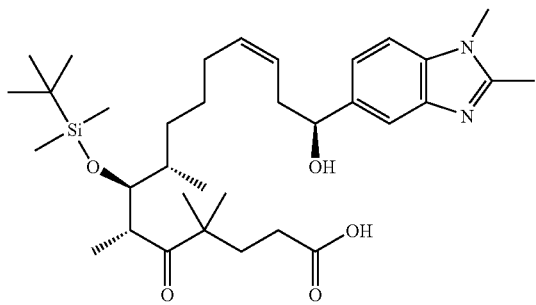

Lithium hydroxide (163 mg) is added to a solution of 19 (700 mg) in a mixture of isopropanol (16 ml) and water (4 ml). The reaction mixture is then warmed up to 60° C. and stirred for 45 min. The mixture is then poured into an Erlenmeyer containing 40 ml of $CH_2Cl_2$ and 40 ml of water. The mixture is then acidified to pH 5 by a slow addition of Hydrochloric acid 1M under vigorous stirring (approx 6.5 ml). The two layers are separated by decantation and the aqueous phase is extracted three times with 20 ml of $CH_2Cl_2$. The organic phases are joined and after drying with magnesium sulfate, removing of the solvents under vacuo, the crude is purified by flash chromatography ($CH_2Cl_2$/Methanol: 95/5 to 90110) to yield 20 as a white foam.

ESI-MS: 601.0 $(M+H)^+$.
Rf=0.43 ($CH_2Cl_2$/MeOH: 90/10).
$^1$H-NMR (400 MHz, $CDCl_3$/ppm): 7.88 (s, 1H), 7.31 (AB system, 2H), 5.62 (m, 1H), 5.47 (m, 1H), 4.84 (dd, 9.5 Hz, 1H), 3.88 (dd, 6.3 Hz, 1H), 3.75 (s, 3H), 3.24 (m, 1H), 2.72-1.88 (m, 8H), 2.65 (s, 3H), 1.54-1.06 (m, 5H), 1.23 (s, 3H), 1.20 (s, 3H), 1.13 (d, 7 Hz, 3H), 0.95 (d, 3H), 0.94 (s, 9H), 0.13 (s, 3H), 0.10 (s, 3H).

(3e)—Compound 21

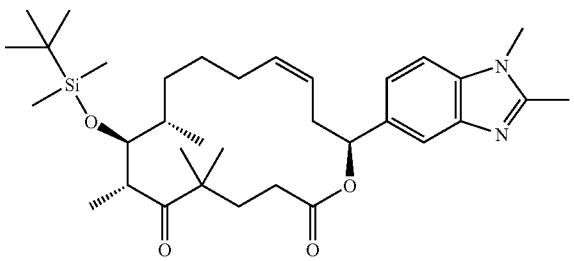

Flask A: To a solution of 20 (473 mg) and Triethylamine (770 μl) in tetrahydrofuran (20 ml) at 0° C., is rapidly added 2,4,6-trichlorobenzoyl chloride (740 μl). After stirring at 0° C. for 15 min, the mixture is allowed to warm up to room temperature and stirred for another 15 minutes.

Flask B: The content of Flask A is slowly added (2 h) to a solution of DMAP (1.15 g) in 600 ml of toluene, under vigorous stirring. After the end of the addition, the mixture is stirred for an additional 30 minutes. The solvents are then removed under vacuo and the residue is purified by flash chromatography (Hexanes/acetone 60/40 to 40/60) to yield 21, as a white foam.

ESI-MS: 583.2 $(M+H)^+$.
Rf=0.31 (Hex/acetone: 50/50).
$^1$H-NMR (400 MHz, $CDCl_3$/ppm): 7.59 (s, 1H), 7.16 (m, 2H), 5.89 (dd, 1H), 5.37 (m, 2H), 3.72 (m, 1H), 3.64 (s, 3H), 3.05 (m, 1H), 2.74 (m, 1H), 2.52 (s, 3H), 2.35 (m, 1H), 2.26-1.63 (m, 6H), 1.42-0.74 (m, 2H), 1.20 (s, 3H), 1.02 (d, 7 Hz, 3H), 0.92 (s, 3H), 0.87 (d, 7 Hz, 3H), 0.84 (s, 9H), 0.05 (s, 3H), 0.0 (s, 3H).

Example 4

3-(1,2-Dimethyl-1H-benzoimidazol-5-yl)-11-hydroxy-8,8,10,12-tetramethyl-4,17-dioxa-bicyclo[14.1.0]heptadecane-5,9-dione (Compound 23)

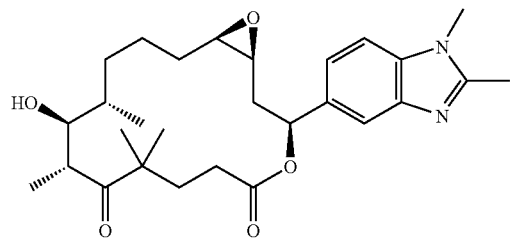

In a 10 ml round bottomed flask are successively introduced distilled water (7 ml), Pyridine (50 μl) and hydrogen peroxide 30% (700 μl). A part of this solution (5 ml) is rapidly added in a solution of 22 (94 mg) in 5 ml of $CH_2Cl_2$ and under vigorous stirring, MTO (20 mg) is added in one portion. After 5 h of stirring, the reaction mixture is quenched by addition of 5 ml of a saturated aqueous NaHCO3 solution. The two layers are separated by decantation and the aqueous phase is extracted twice with $CH_2Cl_2$(20 ml). After drying with magnesium sulfate and removal of the solvent in vacuo, the crude mixture (a 2:1 diastereomeric mixture) is purified by preparative TLC, to finally yield the pure diastereomer 23, as a white powder.

ESI-MS: 485.3 $(M+H)^+$.
Rf-0.40 (Hexane/acetone: 30/70).
$^1$H-NMR (400 MHz, $CDCl_3$/ppm): 7.68 (s, 1H), 7.29 (m, 2H), 6.05 (dd, 10 Hz, 3 Hz, 1H), 3.81 (m, 1H), 3.76 (s, 3H), 3.27 (m, 1H), 3.12 (m, 1H), 2.98 (m, 1H), 2.64 (s, 3H), 2.37-1.35 (m, 13H), 1.30 (s, 3H), 1.22 (d, 7 Hz, 3H), 1.10 (d, 7 Hz, 3H), 1.03 (s, 3H).

Example 5

(Z)-(7R,8S,9S,16S)-16-(1,2-Dimethyl-1H-benzoimidazol-5-yl)-8-hydroxy-5,5,7,9,13-pentamethyl-oxacyclohexadec-13-ene-2,6-dione (29)

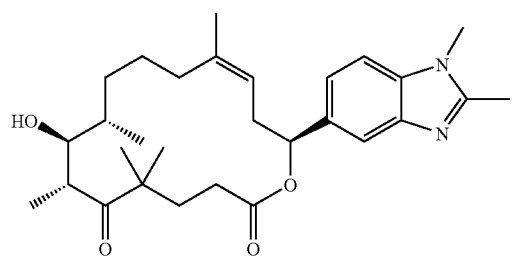

To a solution of 28 (100 mg, 0.167 mmol) in 5 mL $CH_3CN$ and in a Teflon tube is added at rt 1 mL of HF.Pyridine (70/30)

and the reaction mixture is stirred for 3 h at rt. The reaction mixture is washed with a 5% solution of NaHCO$_3$, extracted 3 times with 10 mL AcOEt and then the organic layers are dried (MgSO$_4$). Purification by flash column chromatography (Hexane/Acetone—90/10 to 50/50) afforded 29.

ESI-MS: M(C$_{29}$H$_{42}$N$_2$O$_4$)=482.6, (M+H)$^+$=483.3.

Rf: Hexane/Acetone—30/70: 0.36.

$^1$H NMR (400 MHz, CDCl$_3$): δ=7.62 (s, 1H), 7.20 (m, 2H), 5.87 (m, 1H), 5.20 (m, 1H), 3.72 (m, 1H), 3.72 (s, 3H), 3.21 (m, 1H), 2.92 (m, 2H), 2.60 (s, 3H), 2.30 (m, 2H), 2.10 (m, 2H), 1.90 (m, 2H), 1.63 (s, 3H), 1.30 (m, 2H), 1.22 (s, 3H), 1.18 (d, 3H), 1.04 (d, 3H), 0.98 (s, 3H).

(5a)—Compound 25

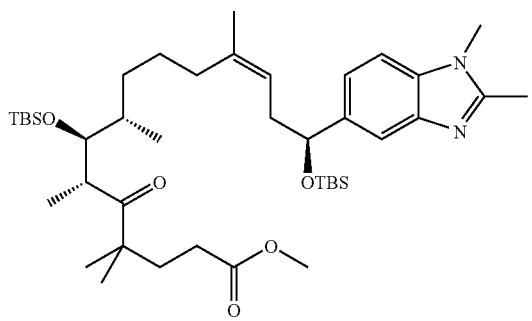

To a 0.5M solution of 9-BBN in 3 mL THF (3.85 mL, 1.913 mmol) is added dropwise 7 (0.38 g, 0.96 mmol) in 3 mL THF at rt. After 30 min TLC analysis revealed the complete consumption of the starting olefin. In a separate flask, containing vinyl iodide 24 (0.45 g, 0.96 mmol) in 4 mL DMF were added successively, CsCO$_3$ (0.62 g, 1.91 mmol), AsPh$_3$ (59 mg, 0.19 mmol), Pd(dppf)$_2$Cl$_2$ (140 mg, 0.19 mmol) and H$_2$O (0.51 mL, 28.7 mmol). In first solution is added H$_2$O (0.17 mL, 9.5 mmol) to quench the excess 9-BBN and the alkyl borane solution is added rapidly by syringe to the solution containing the vinyl iodide. The reaction mixture is stirred at rt for 2 h and quenched with H$_2$O, extracted 3 times with 25 mL Et$_2$O. The combined organic layers are dried (MgSO$_4$) and concentrated in vacuum. Purification by flash column chromatography (Hexane/Acetone—90/10 to 70/30) afforded 25 as an oil.

ESI-MS: M(C$_{42}$H$_{74}$N$_2$O$_5$Si$_2$)=743.2, (M+H)$^+$=743.4.

Rf: Hexane/Acetone—50/50: 0.54.

$^1$H NMR (400 MHz, CDCl$_3$): δ=7.60 (s, 1H), 7.22 (m, 2H), 5.20 (m, 1H), 4.75 (t, 1H), 3.80 (m, 1H), 3.75 (s, 3H), 3.67 (s, 3H), 3.18 (m, 1H), 2.60 (s, 3H), 2.40 (m, 2H), 2.22 (m, 2H), 1.90 (m, 2H), 1.80 (m, 2H), 1.65 (s, 3H), 1.30 (m, 2H), 1.20 (s, 3H), 1.10 (s, 3H), 1.05 (d, 3H), 0.93 (s, 9H), 0.92 (d, 3H), 0.91 (s, 9H), 0.09 (s, 6H), 0.03 (s, 3H), −0.14 (s, 3H).

(5b)—Compound 26

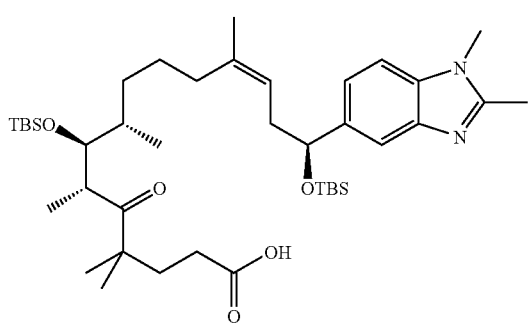

To a solution of 25 (0.5 g, 0.67 mmol) in 20 mL i-PrOH/H$_2$O—4/1 is added LiOH (97 mg, 4 mmol) and the mixture is heated at 60° C. for 3 h. After cooling to rt, the solution is quenched with a saturated solution of NH$_4$Cl, extracted 3 times with 25 mL CH$_2$Cl$_2$. The combined organic layers are dried (MgSO$_4$) and concentrated in vacuum. The crude product is used directly in the next step.

ESI-MS: M(C$_{41}$H$_{72}$N$_2$O$_5$Si$_2$)=729.2, (M+H)$^+$=729.3.

Rf: Hexane/Acetone—30/70: 0.57.

$^1$H NMR (400 MHz, CD$_3$OD): δ=7.50 (s, 1H), 7.38 (d, 1H), 7.21 (d, 1H), 5.20 (m, 1H), 4.78 (t, 1H), 3.78 (m, 1H), 3.78 (s, 3H), 3.20 (m, 1H), 2.60 (s, 3H), 2.40 (m, 2H), 2.08 (m, 2H), 1.93 (m, 2H), 1.80 (m, 2H), 1.62 (s, 3H), 1.30 (m, 4H), 1.18 (s, 3H), 1.16 (s, 3H), 1.05 (d, 3H), 0.92 (s, 9H), 0.92 (d, 3H), 0.91 (s, 9H), 0.06 (s, 6H), 0.05 (s, 3H), −0.17 (s, 3H).

(5c)—Compound 27

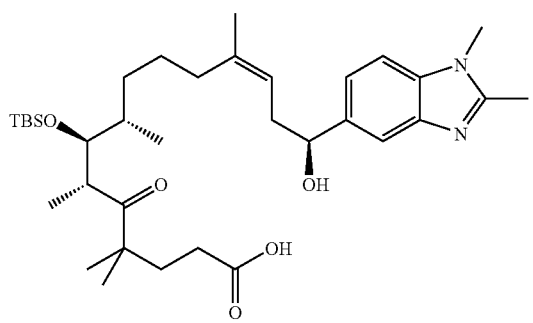

To a solution of 26 (0.44 g, 0.6 mmol) in 5 mL THF at rt is added a 1M solution of TBAF (1.8 mL, 1.8 mmol) and reaction mixture is stirred at rt overnight. The reaction mixture is washed with a saturated solution of NH$_4$Cl, extracted 3 times with 10 mL CH$_2$Cl$_2$ and then the organic layers are dried (MgSO$_4$). Purification by flash column chromatography (Hexane/Et$_2$O—90/10 to 50/50) afforded 27 as a colourless oil.

ESI-MS: M(C$_{35}$H$_{58}$N$_2$O$_5$Si)=614.9, (M+H)$^+$=615.3.

Rf: Hexane/Acetone—30/70: 0.24.

$^1$H NMR (400 MHz, CD$_3$OD): δ=7.52 (s, 1H), 7.39 (d, 1H), 7.26 (d, 1H), 5.18 (m, 1H), 4.69 (t, 1H), 3.78 (m, 1H), 3.76 (s, 3H), 3.20 (m, 1H), 2.60 (s, 3H), 2.48 (m, 2H), 2.12 (m, 2H), 1.94 (m, 2H), 1.78 (m, 2H), 1.62 (s, 3H), 1.30 (m, 4H), 1.15 (s, 3H), 1.06 (s, 3H), 1.05 (d, 3H), 0.89 (s, 9H), 0.89 (d, 3H), 0.05 (s, 3H), 0.04 (s, 3H).

(5d)—Compound 28: (Z)-(7R,8S,9S,16S)-8-(tert-Butyl-dimethyl-silanyloxy)-16-(1,2-dimethyl-1H-benzoimidazol-5-yl)-5,5,7,9,13-pentamethyl-oxacyclohexadec-13-ene-2,6-dione

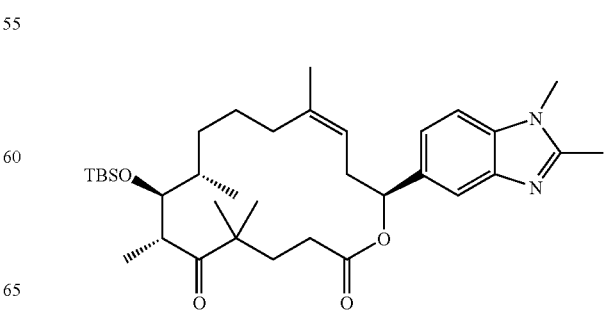

To a solution of 27 (120 mg, 0.195 mmol) in 5 mL THF at 0° C. is added triethylamine (0.163 mL, 1.17 mmol) followed by trichlorobenzylchloride (0.152 mL, 0.975 mmol). After stirring for 20 min at rt, the solution is diluted with 20 mL dry toluene and the resulting solution is added slowly in 1 h to a previously prepared solution of DMAP (0.24 g, 1.95 mmol) in 150 mL toluene. The reaction mixture is stirred at rt for 30 min and then concentrated in vacuum. The crude product is purified by flash column chromatography (Hexane/Acetone—90/10 to 70/30) to afford 28 as an oil.

ESI-MS: $M(C_{35}H_{56}N_2O_4Si)=596.9$, $(M+H)^+=597.3$.

Rf: Hexane/Acetone—70/30: 0.18.

$^1$H NMR (400 MHz, CDCl$_3$) for major compound: δ=7.62 (s, 1H), 7.20 (m, 2H), 5.90 (m, 1H), 5.18 (m, 1H), 3.79 (m, 1H), 3.70 (s, 3H), 3.17 (m, 1H), 2.60 (s, 3H), 2.30 (m, 2H), 2.10 (m, 2H), 1.80 (m, 2H), 1.63 (s, 3H), 1.30 (m, 2H), 1.23 (s, 3H), 1.08 (d, 3H), 1.00 (s, 3H), 0.95 (d, 3H), 0.90 (s, 9H), 0.10 (s, 3H), 0.07 (s, 3H).

Example 6

(1S,3S,10R,11S,12S,16R)-3-(1,2-Dimethyl-1H-benzoimidazol-5-yl)-11-hydroxy-8,8,10,12,16-pentamethyl-4,17-dioxa-bicyclo[14.1.0]heptadecane-5,9-dione (30)

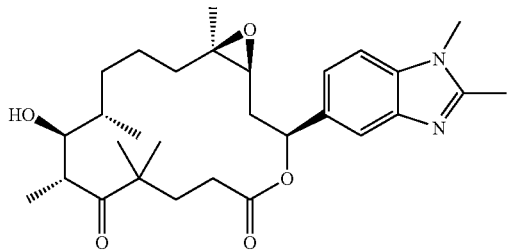

To a solution of 29 (30 mg, 0.062 mmol) in 2 mL of CH$_2$Cl$_2$ at rt is added 1 mL of a solution H$_2$O$_2$/H$_2$O/Pyridine—16/140/1 and MTO (7.8 mg, 0.031 mmole). The reaction mixture is stirred at rt for 30 min and then is quenched with a saturated solution of NH$_4$Cl and extracted 3 times with 10 mL CH$_2$Cl$_2$. The combined organic layers are dried (MgSO$_4$) and concentrated in vacuum. Purification by flash column chromatography (Hexane/Acetone—90/10 to 70/30) afforded 30 in more than 10/1 ratio in favour of desired epoxide.

ESI-MS: $M(C_{29}H_{42}N_2O_5)=498.6$, $(M+H)^+=498.9$.

Rf: Hexane/Acetone—30/70: 0.25.

$^1$H NMR (400 MHz, CDCl$_3$): δ=7.62 (s, 1H), 7.21 (m, 2H), 6.00 (m, 1H), 3.78 (m, 1H), 3.72 (s, 3H), 3.22 (m, 1H), 2.91 (m, 2H), 2.60 (s, 3H), 2.59 (m, 1H), 2.30 (m, 2H), 2.10 (m, 2H), 1.90 (m, 2H), 1.40 (m, 4H), 1.27 (s, 3H), 1.21 (s, 3H), 1.15 (d, 3H), 1.04 (d, 3H), 0.99 (s, 3H).

Example 7

(E)-(7R,8S,9S,16S)-16-(1,2-Dimethyl-1H-benzoimidazol-5-yl)-8-hydroxy-5,5,7,9-tetramethyl-oxacyclohexadec-13-ene-2,6-dione (37)

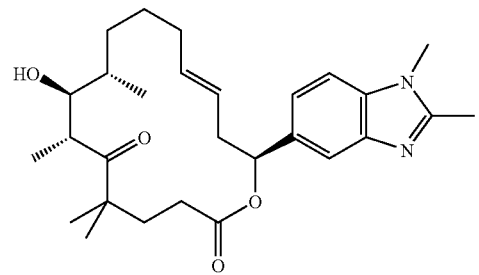

To a solution of 36 (110 mg, 0.188 mmol) in 5 mL CH$_3$CN and in a Teflon tube is added at rt 1 mL of HF.Pyridine (70/30) and the reaction mixture is stirred for 2 h at rt. The reaction mixture is washed with a 5% solution of NaHCO$_3$, extracted 3 times with 10 mL AcOEt and then the organic layers are dried (MgSO$_4$). Purification by flash column chromatography (Hexane/Acetone—90/10 to 50/50) afforded 37 as a colourless oil.

ESI-MS: $M(C_{28}H_{40}N_2O_4)=468.6$, $(M+H)^+=469.3$.

Rf: Hexane/Acetone—30/70: 0.35.

$^1$H NMR (400 MHz, CDCl$_3$): δ=7.80 (s, 1H), 7.25 (m, 2H), 6.10 (m, 1H), 5.60 (m, 1H), 5.50 (m, 1H), 3.80 (m, 1H), 3.80 (s, 3H), 3.30 (m, 1H), 2.60 (s, 3H), 2.55 (m, 2H), 2.40 (m, 2H), 2.20 (m, 2H), 1.90 (m, 4H), 1.60 (m, 4H), 1.15 (s, 6H), 1.10 (d, 3H), 0.95 (d, 3H).

(7a)—Compound 31

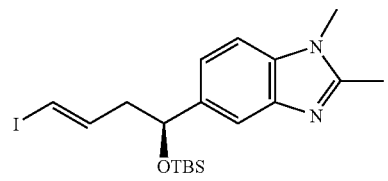

To a solution of CrCl$_2$ (3.0 g, 24.06 mmol) in 10 mL THF at rt, is added dropwise over 30 min a mixture of 16 (1.0 g, 3.0 mmol) and CHI$_3$ (2.4 g, 6.0 mmol) in 60 mL of Dioxane. The reaction mixture is stirred 3 h at rt and quenched with 20 mL H$_2$O, extracted 3 times with 20 mL Et$_2$O and 3 times with 20 mL AcOEt. The combined organic layers are dried (MgSO$_4$) and concentrated in vacuum. Purification by flash column chromatography (CH$_2$Cl$_2$/Acetone—100/0 to 0/100) afforded 31 in a 5/1 ratio.

ESI-MS: $M(C_{19}H_{29}N_2OSiI)=456.4$, $(M+H)^+=457.0$.

Rf: Acetone—100: 0.50.

$^1$H NMR (400 MHz, CDCl$_3$): δ=7.60 (s, 1H), 7.20 (m, 2H), 6.50 (m, 1H), 6.00 (dt, 1H), 4.80 (m, 1H), 3.70 (s, 3H), 2.80 (s, 3H), 2.40 (m, 2H), 0.95 (s, 9H), 0.05 (s, 3H), −0.18 (s, 3H).

(7b)—Compound 32

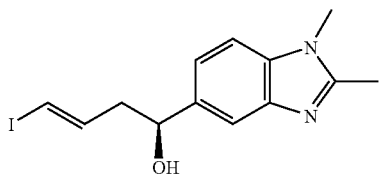

To a solution of 31 (1.0 g, 2.191 mmol) in 100 mL of a CH$_2$Cl$_2$/MeOH—1/1 solution, is added CSA (2.24 g, 9.64 mmol) and the reaction mixture is stirred 2 days at rt. The mixture is quenched with NaHCO$_3$ (5%) solution until pH-7 and extracted 3 times with 25 mL AcOEt. The combined organic layers are dried (MgSO$_4$) and concentrated in vacuum. Purification by flash column chromatography (CH$_2$Cl$_2$/MeOH—100/0 to 95/5) afforded 32. Crystallization in CH$_2$Cl$_2$/Hexane—1/1 with 3 drops of MeOH afforded 32 in a 15/1 ratio as white crystals.

ESI-MS: M(C$_{13}$H$_{15}$N$_2$OI)=342.2, (M+H)$^+$=343.0.

Rf: Hexane/Acetone—50/50: 0.25.

$^1$H NMR (400 MHz, CDCl$_3$): δ=7.60 (s, 1H), 7.20 (m, 2H), 6.50 (m, 1H), 6.10 (d, 1H), 4.80 (m, 1H), 3.75 (s, 3H), 2.65 (s, 3H), 2.55 (m, 2H).

(7c)—Compound 33

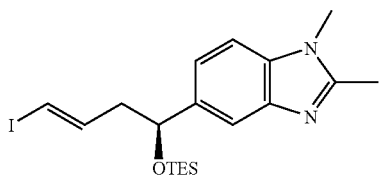

To a solution of 32 (0.6 g, 1.753 mmol) in 8 mL DMF at 0° C. is added imidazole (0.36 g, 5.26 mmol) followed by TESCl (0.44 mL, 2.63 mmol). The mixture is stirred 1 h30 at 0° C. and then is quenched with H$_2$O, extracted 3 times with 20 mL Et$_2$O. The combined organic layers are dried (MgSO$_4$) and concentrated in vacuum. Purification by flash column chromatography (Hexane/Acetone—90/10) afforded 33 as colourless oil.

ESI-MS: M(C$_{19}$H$_{29}$N$_2$OSiI)=456.4, (M+H)$^+$=457.1.

Rf: Hexane/Acetone—50/50: 0.67.

$^1$H NMR (400 MHz, CDCl$_3$): δ=7.58 (s, 1H), 7.20 (m, 2H), 6.50 (m, 1H), 6.00 (dt, 1H), 4.80 (m, 1H), 3.70 (s, 3H), 2.80 (s, 3H), 2.40 (m, 2H), 0.95 (t, 9H), 0.50 (q, 6H).

(7d)—Compound 34

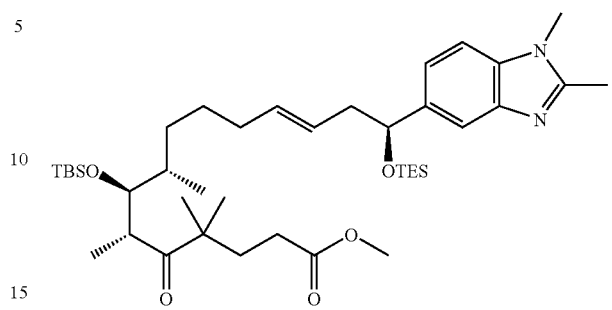

To a 0.5M solution of 9-BBN in 2 mL THF (6.57 mL, 3.286 mmol) is added dropwise 7 (0.63 g, 1.577 mmol) in 5 mL THF at rt. After 2 h TLC analysis revealed the complete consumption of the starting olefin. In a separate flask, containing vinyl iodide (0.6 g, 1.314 mmol) in 5 mL DMF were added successively, CsCO$_3$ (0.85 g, 2.63 mmol), AsPh$_3$ (80 mg, 0.263 mmol), Pd(dppf)$_2$Cl$_2$ (192 mg, 0.263 mmol) and H$_2$O (0.71 mL, 39.43 mmol). In first solution is added H$_2$O (0.24 mL, 13.14 mmol) to quench the excess 9-BBN and the alkyl borane solution is added rapidly by syringe to the solution containing the vinyl iodide 33. The reaction mixture is stirred at rt for 2 h and quenched with H$_2$O, extracted 3 times with 20 mL CH$_2$Cl$_2$. The combined organic layers are dried (MgSO$_4$) and concentrated in vacuum. Purification by flash column chromatography (Hexane/Acetone—90/10 to 50/50) afforded 34 as an oil.

ESI-MS: M(C$_{34}$H$_{72}$N$_2$O$_5$Si$_2$)=729.2, (M+H)$^+$=730.2.

Rf: Hexane/Acetone—70/30: 0.27.

$^1$H NMR (400 MHz, CDCl$_3$): δ=7.60 (s, 1H), 7.20 (m, 2H), 5.40 (m, 2H), 4.70 (t, 1H), 3.80 (m, 1H), 3.75 (s, 3H), 3.70 (s, 3H), 3.15 (m, 1H), 2.60 (s, 3H), 2.40 (m, 2H), 2.20 (m, 2H), 1.90 (m, 2H), 1.80 (m, 6H), 1.30 (m, 4H), 1.20 (s, 3H), 1.10 (s, 3H), 1.05 (d, 3H), 0.95 (d, 3H), 0.93 (s, 9H), 0.85 (t, 9H), 0.50 (q, 6H), 0.05 (s, 6H).

(7e)—Compound 35

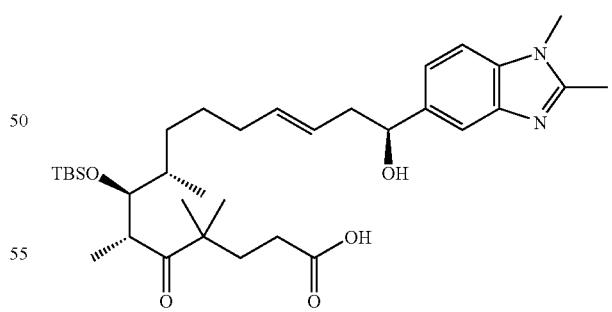

To a solution of 34 (0.27 g, 0.37 mmol) in 10 mL i-PrOH/H$_2$O—4/1 is added LiOH (54 mg, 2.22 mmol) and the mixture is heated at 60° C. for 6 h. After cooling to rt, the solution is quenched with a saturated solution of NH$_4$Cl, extracted twice with 10 mL CH$_2$Cl$_2$ and twice with 10 mL AcOEt. The combined organic layers are dried (MgSO$_4$) and concentrated in vacuum. Purification by flash column chromatography (CH$_2$Cl$_2$/MeOH—95/5 to 70/30) afforded 35 as a colourless oil.

ESI-MS: M($C_{34}H_{56}N_2O_5Si$)=600.9, (M+H)$^+$=601.2.
Rf: Hexane/Acetone—30/70: 0.27.
$^1$H NMR (400 MHz, CDCl$_3$): δ=7.65 (s, 1H), 7.25 (m, 2H), 5.50 (m, 1H), 5.30 (m, 1H), 4.80 (t, 1H), 3.80 (m, 1H), 3.70 (s, 3H), 3.20 (m, 1H), 2.60 (s, 3H), 2.45 (m, 2H), 2.25 (m, 2H), 1.90 (m, 2H), 1.80 (m, 6H), 1.40 (m, 4H), 1.20 (s, 3H), 1.10 (s, 3H), 1.05 (d, 3H), 0.95 (d, 3H), 0.94 (s, 9H), 0.05 (s, 6H).

(7f)—Compound 36: (E)-(7R,8S,9S,16S)-16-(1,2-Dimethyl-1H-benzoimidazol-5-yl)-5,5,7,8,9-pentamethyl-oxacyclohexadec-13-ene-2,6-dione

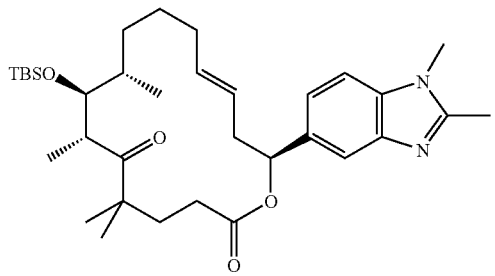

To a solution of 35 (160 mg, 0.266 mmol) in 7 mL THF at 0° C. is added triethylamine (0.22 mL, 1.6 mmol) followed by trichlorobenzylchloride (0.21 mL, 1.33 mmol). After stirring for 20 min at rt, the solution is diluted with 20 mL dry toluene and the resulting solution is added slowly in 1 h to a previously prepared solution of DMAP (0.32 mg, 2.66 mmol) in 170 mL toluene. The reaction mixture is stirred at rt for 1 h and then concentrated in vacuum. The crude product is purified by flash column chromatography (Hexane/Acetone—90/10 to 50/50) to afford 36 as a colourless oil.
ESI-MS: M($C_{34}H_{54}N_2O_4Si$)=582.9, (M+H)$^+$=583.2.
Rf: Hexane/Acetone—30/70: 0.38.
$^1$H NMR (400 MHz, CDCl$_3$): δ=7.65 (s, 1H), 7.20 (2 s, 2H), 6.05 (m, 1H), 5.60 (m, 1H), 5.50 (m, 1H), 3.80 (m, 1H), 3.70 (s, 3H), 3.20 (m, 1H), 2.60 (s, 3H), 2.40 (m, 2H), 2.25 (m, 2H), 2.00 (m, 2H), 1.80 (m, 6H), 1.40 (m, 4H), 1.20 (s, 3H), 1.20 (s, 3H), 1.15 (d, 3H), 0.95 (d, 3H), 0.94 (s, 9H), 0.10 (s, 3H), 0.05 (s, 3H).

Example 8

(1S,3S,10R,11S,12S,16S)-3-(1,2-Dimethyl-1H-benzoimidazol-5-yl)-11-hydroxy-8,8,10,12-tetramethyl-4,17-dioxa-bicyclo[14.1.0]heptadecane-5,9-dione (38)

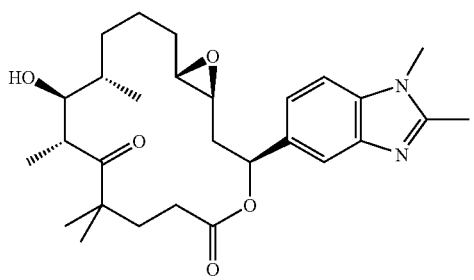

To a solution of 37 (30 mg, 0.064 mmol) in 1 mL CH$_3$CN/DMM—1/1 at rt were added successively 0.6 mL of a buffer solution (Na$_2$B$_4$O$_7$.10 H$_2$O [0.05M] in Na$_2$EDTA [4.10$^{-4}$M]), Bu$_4$N(HSO$_4$) (0.9 mg, 0.0025 mmol) and fructose-derived ketone (13.2 mg, 0.051 mmol). The reaction mixture is cooled to 0° C. and were added separately, in a same time over 1 h30, Oxone® (55.1 mg, 0.089 mmol) in 0.8 mL Na$_2$EDTA and K$_2$CO$_3$ (51.3 mg, 0.371 mmol) in 0.8 mL H$_2$O. The solution is stirred at 0° C. for 3 h and then is quenched with H$_2$O, extracted 3 times with 10 mL AcOEt. The combined organic layers are dried (MgSO$_4$) and concentrated in vacuum. Purification by flash column chromatography (Hexane/Acetone/MeOH—70/30/0 to 45/50/5) afforded 38, 76% conversion.
ESI-MS: M($C_{28}H_{40}N_2O_4$)=484.6, (M+H)$^+$=485.3.
Rf: Hexane/Acetone—30/70: 0.22.
$^1$H NMR (400 MHz, CDCl$_3$): δ=7.60 (s, 1H), 7.25 (m, 2H), 6.10 (m, 1H), 3.80 (m, 1H), 3.75 (s, 3H), 3.25 (m, 1H), 2.90 (m, 2H), 2.60 (s, 3H), 2.40 (m, 2H), 2.35 (m, 2H), 2.20 (m, 2H), 1.90 (m, 6H), 1.60 (m, 4H), 1.15 (s, 6H), 1.20 (d, 3H), 1.00 (d, 3H).

Example 9

16-(1,2-Dimethyl-1H-benzoimidazol-5-yl)-4,8-dihydroxy-5,5,7,9-tetramethyl-oxacyclohexadec-13-ene-2,6-dione (Compound 43)

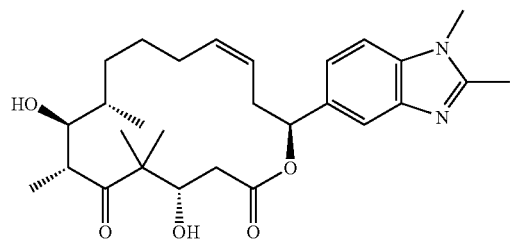

To a 50 ml plastic tube, equipped with a magnetic stir bar, are successively added 42 (170 mg) and 10 ml of acetonitrile. To this solution is rapidly added HF-Pyridine complex (2 ml). The reaction is monitored by TLC (CH$_2$Cl$_2$/MeOH: 95/5) and the mixture is stirred at room temperature for 20 h. The reaction mixture is then carefully added drop wise to an Erlenmeyer containing CH$_2$Cl$_2$ (30 ml) and (30 ml) and saturated aqueous sodium bicarbonate. The pH of the aqueous phase is adjusted to 9 by addition of pure sodium bicarbonate. The two layers are then separated by decantation and the aqueous phase is extracted three times with CH$_2$Cl$_2$ (30 ml). After drying with magnesium sulfate, the solvents are removed under vacuo and the crude mixture is purified by flash chromatography (CH$_2$Cl$_2$/methanol: 95/5 to 90/10) to finally give 43 as a white solid.
ESI-MS: 485.3 (M+H)$^+$.
Rf=0.24 (CH$_2$Cl$_2$/MeOH: 95/5).
$^1$H-NMR (400 MHz, CD$_3$OD/ppm): 7.62 (s, 1H), 7.37 (AB, 10 Hz, 2H), 5.88 (m, 1H), 5.50 (m, 2H), 4.27 (m, 1H), 3.77 (s, 3H), 3.68 (m, 1H), 3.27 (q, 8Hz, 1H), 2.95 (m, 1H), 2.59 (s, 3H), 2.50-2.28 (m, 4H), 2.01 (m, 1H), 1.69 (m, 1H), 1.60-1.43 (m, 2H), 1.37-1.10 (m, 2H), 1.30 (s, 3H), 1.21 (d, 8 Hz, 3H), 1.05 (d, 7 Hz, 3H), 1.02 (s, 3H), 0.9 (m, 1H).

(9a)—Compound 40

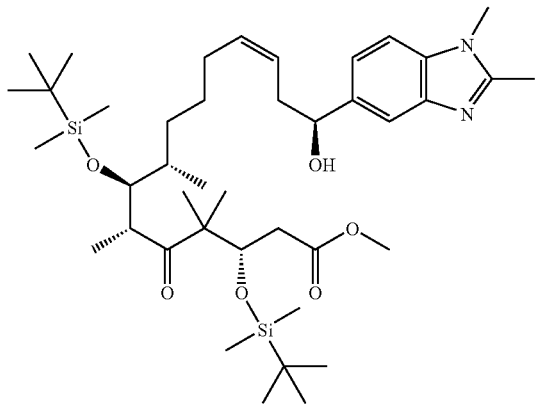

Flask A: To a solution of 39 (265 mg) in 3.5 ml THF is added 9-BBN (2 ml of a 0.5M solution in THF) drop wise at 0° C. After the end of the addition, the ice bath is removed and the reaction mixture is allowed to warm up to room temperature. The reaction is monitored by TLC and is complete after 100 minutes. The excess of 9-BBN is quenched by addition of 50 μl of distilled water.

Flask B: In a 25 ml three-necked round bottomed flask, are successively added the vinyl iodide 18 (142 mg) and 5 ml of DMF. The solution is cooled down to 0° C. and Cesium carbonate (234 mg), triphenylarsine (25 mg), the Palladium catalyst (68 mg) and distilled water (200 μl) are successively added. The content of Flask A is then rapidly added (30 sec) under vigorous stirring. After 10 minutes at 0° C., the ice bath is removed and the reaction mixture is allowed to warm up to room temperature. The reaction is monitored by MS and is complete after 1 h15. The mixture is then poured in a 100 ml Erlenmeyer containing 50 ml of diethyl ether and 50 ml of a saturated aqueous ammonium chloride. The two layers are separated by decantation and the aqueous phase is extracted twice with 50 ml of diethyl ether. The organic phases are joined and dried with magnesium sulfate. Evaporation of the solvents under vacuo yielded a brown oil which is purified by flash chromatography (Hexanes/Acetone: 80/20 to 60/40) to finally yield 40 as a thick yellow oil.

ESI-MS: 745.2 (M+H)$^+$.

Rf=0.15 (Hex/Acetone: 70/30).

$^1$H-NMR (400 MHz, CDCl$_3$/ppm): 7.69 (s, 1H), 7.38 (AB, 2H), 5.53 (m, 1H), 5.37 (m, 1H), 4.81 (dd, 1H), 4.39 (dd, 1H), 3.81 (s, 3H), 3.77 (dd, 1H), 3.70 (s, 3H), 3.13 (m, 1H), 2.79 (s, 3H), 2.69-2.46 (m, 2H), 2.42 (A of ABX, 1H), 2.27 (B of ABX, 1H), 2.02 (m, 2H), 1.43-1.0 (m, 6H), 1.24 (s, 3H), 1.07 (s, 3H), 1.04 (d, 7Hz, 3H), 0.91 (s, 9H), 0.89 (d, 7Hz, 3H), 0.88 (s, 9H), 0.10 (s, 3H), 0.06 (s, 6H), 0.03 (s, 3H).

(9b)—Compound 41

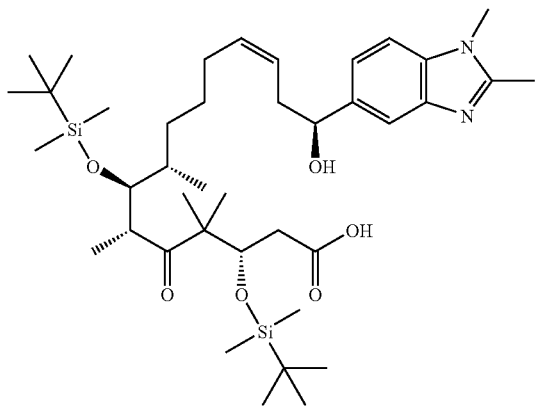

Lithium hydroxide (39 mg) is added to a solution of 40 (200 mg) in a mixture of isopropanol (4.8 ml) and water (1.2 ml). The reaction mixture is then warmed up to 60° C. and stirred for 2 h30. The mixture is then poured into an Erlenmeyer containing 40 ml of CH$_2$Cl$_2$ and 30 ml of water. The mixture is then acidified to pH 5 by a slow addition of Hydrochloric acid 0.1 N under vigorous stirring (approx 16 ml). The two layers are separated by decantation and the aqueous phase is extracted three times with 20 ml of CH$_2$Cl$_2$. The organic phases are joined and after drying with magnesium sulfate, removing of the solvents under vacuo, the crude is purified by flash chromatography (Hexanes/acetone: 50/50 to 0/100) to yield 41, as a white foam.

ESI-MS: 731.3 (M+H)$^+$.

Rf=0.12 (CH$_2$Cl$_2$/MeOH: 95/5).

$^1$H-NMR (400 MHz, CD$_3$OD/ppm): 7.53 (s, 1H), 7.34 (AB, 2H), 5.39 (m, 2H), 4.72 (t, 1H), 4.33 (dd, 1H), 3.77 (s, 3H), 3.74 (dd, 1H), 3.21 (m, 1H), 2.60 (s, 3H), 2.54 (m, 2H), 2.43 (A of ABX, 1H), 2.18 (B of ABX, 1H), 1.93 (m, 2H), 1.44-0.97 (m, 6H), 1.22 (s, 3H), 1.06 (s, 3H), 1.05 (d, 3H), 0.91 (s, 9H), 0.88 (s, 9H), 0.87 (d, 3H), 0.10 (s, 3H), 0.07 (s, 3H), 0.06 (s, 3H), 0.05 (s, 3H).

(9c)—Compound 42

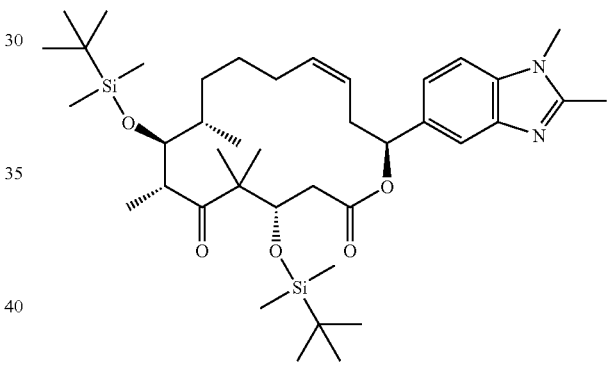

Flask A: To a solution of 41 (300 mg) and Triethylamine (345 μl) in tetrahydrofuran (10 ml) at 0° C., is rapidly added 2,4,6-trichlorobenzoyl chloride (320 μl). After stirring at 0° C. for 15 min, the mixture is allowed to warm up to room temperature and stirred for another 15 minutes.

Flask B: The content of Flask A is slowly added (1 h30) to a solution of DMAP (600 mg) in 300 ml of toluene, under vigorous stirring. After the end of the addition, the mixture is stirred for an additional 30 minutes. The solvents are then removed under vacuo and the residue is purified by flash chromatography (Hexanes/acetone 60/40 to 40/60) to yield the desired product 42, as a white foam.

ESI-MS: 713.1 (M+H)$^+$.

Rf=0.37 (CH$_2$Cl$_2$/MeOH: 95/5).

$^1$H-NMR (400 MHz, CD$_3$OD/ppm): 7.56 (s, 1H), 7.31 (AB, 2H), 5.62 (bd, 10 Hz, 1H), 5.60-5.40 (m, 2H), 3.99 (d, 9 Hz, 1H), 3.92 (d, 8 Hz, 1H), 3.20-2.67 (m, 4H), 2.60 (s, 3H), 2.16 (m, 1H), 1.93 (m, 1H), 1.66 (m, 2H), 1.3-0.8 (m, 5H), 1.19 (s, 3H), 1.13 (s, 3H), 1.12 (d, 3H), 1.01 (d, 7 Hz, 3H), 0.98 (s, 9H), 0.88 (s, 9H), 0.16 (s, 3H), 0.14 (s, 3H), 0.12 (s, 3H), −0.04 (s, 3H).

Example 10

3-(1,2-Dimethyl-1H-benzoimidazol-5-yl)-7,11-dihydroxy-8,8,10,12-tetramethyl-4,17-dioxa-bicyclo[14.1.0]heptadecane-5,9-dione (Compound 44)

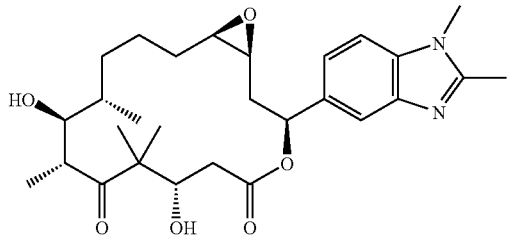

In a 10 ml round bottomed flask are successively introduced distilled water (7 ml), Pyridine (50 µl) and hydrogen peroxide 30% (700 µl). A part of this solution (500 µl) is rapidly added in a solution of 43 (57 mg) in 2 ml of $CH_2Cl_2$ and under vigorous stirring, MTO (2 mg) is added in one portion. After 5 h of stirring, the reaction mixture is added dropwise to an Erlenmeyer containing methylene chloride (20 ml), distilled water (20 ml) and sodium bicarbonate (1 g) The two layers are separated by decantation and the aqueous phase is extracted twice with $CH_2Cl_2$ (20 ml). After drying with magnesium sulfate and removal of the solvent in vacuo, the crude mixture (a 2:1 diastereomeric mixture) is purified by preparative HPLC, to finally yield the pure diastereomer 44, as a white powder.

ESI-MS: 501.0 $(M+H)^+$.

Rf=0.40 ($CH_2Cl_2$/MeOH: 90/10).

$^1$H-NMR (400 MHz, DMSO-d6/ppm): 7.57 (s, 1H), 7.40 (A of AB, 8 Hz, 1H) 7.26 (B of AB, 8 Hz, 1H), 5.92 (bd, 9 Hz, 1H), 5.10 (bd, 6 Hz, 1H), 4.47 (bd, 6 Hz, 1H), 3.94 (m, 1H), 3.72 (s, 3H), 3.51 (m, 1H), 3.13 (m, 2H), 2.88 (m, 1H), 2.58-2.34 (m, 2H), 2.52 (s, 3H), 2.16 (m, 1H), 1.98 (m, 1H), 1.77-1.10 (m, 5H) 1.15 (s, 3H), 1.05 (d, 6 Hz, 3H), 0.93 (s, 3H), 0.92 (d, 3H).

Example 11

(E)-(4S,7R,8S,9S,16S)-16-(1,2-Dimethyl-1H-benzoimidazol-5-yl)-4,8-dihydroxy-5,5,7,9-tetramethyl-oxacyclohexadec-13-ene-2,6-dione (48)

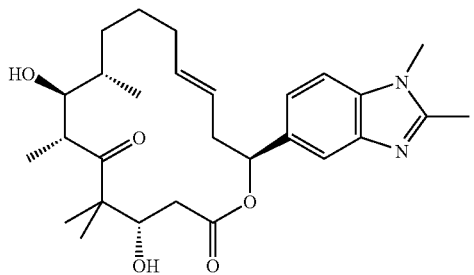

To a solution of 47 (80 mg, 0.112 mmol) in 5 mL $CH_3CN$ and in a Teflon tube is added at rt 1 mL of HF.Pyridine (70/30) and the reaction mixture is stirred 6 h at rt. The reaction mixture is washed with a 5% solution of $NaHCO_3$ (pH-5), extracted 3 times with 10 mL AcOEt and then the organic layers are dried ($MgSO_4$). Purification by flash column chromatography (Hexane/Acetone—50/50 to 0/100) afforded 48 as white crystals.

ESI-MS: $M(C_{28}H_{40}N_2O_5)$=484.6, $(M+H)^+$=485.2.

Rf: Hexane/Acetone—30/70: 0.18.

$^1$H NMR (400 MHz, $CD_3OD$): δ=7.62 (s, 1H), 7.51 (d, 1H), 7.38 (d, 1H), 6.01 (dd, 1H), 5.57 (m, 1H), 5.33 (m, 1H), 4.60 (dd, 1H), 3.90 (s, 3H), 3.66 (dd, 1H), 3.42 (m, 1H), 2.68 (m, 2H), 2.65 (s, 3H), 2.50 (m, 2H), 2.24 (m, 1H), 1.90 (m, 1H), 1.69 (m, 2H), 1.33 (m, 2H), 1.30 (d, 3H), 1.17 (s, 3H), 1.02 (s, 3H), 1.00 (d, 3H).

(11a)—Compound 45

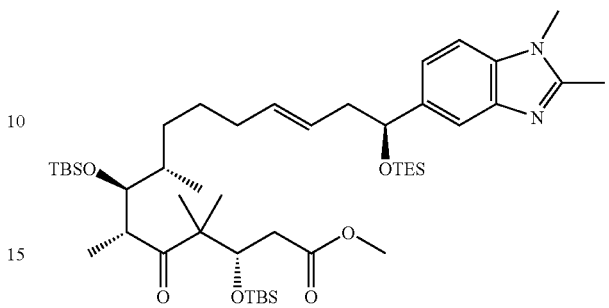

To a 0.5M solution of 9-BBN in 10 mL THF (6.3 mL, 3.149 mmol) is added dropwise 39 (0.8 g, 1.512 mmol) in 5 mL THF at rt. After 2 h TLC analysis revealed the complete consumption of the starting olefin. In a separate flask, containing 33 (0.575 g, 1.260 mmol) in 10 mL DMF were added successively, $Cs_2CO_3$ (0.82 g, 2.519 mmol), $AsPh_3$ (77 mg, 0.251 mmol), $Pd(dppf)_2Cl_2$ (184 mg, 0.251 mmol) and $H_2O$ (0.68 mL, 37.6 mmol). In first solution is added $H_2O$ (226 µL, 12.6 mmol) to quench the excess 9-BBN and the alkyl borane solution is added rapidly by syringe to the solution containing 39. The reaction mixture is stirred at rt overnight and quenched with $H_2O$, extracted 3 times with 30 mL $Et_2O$. The combined organic layers are dried ($MgSO_4$) and concentrated in vacuum. Purification by flash column chromatography (Hexane/Acetone—90/10 to 70/30) afforded 45 as colourless oil.

ESI-MS: $M(C_{47}H_{86}N_2O_6Si_3)$=859.5, $(M)^+$=859.3.

Rf: Hexane/Acetone—50/50: 0.73.

$^1$H NMR (400 MHz, $CDCl_3$): δ=7.60 (s, 1H), 7.20 (m, 2H), 5.40 (m, 2H), 4.71 (m, 1H), 4.20 (m, 1H), 3.80 (m, 1H), 3.70 (s, 3H), 3.67 (s, 3H), 3.17 (m, 1H), 2.60 (s, 3H), 2.40 (m, 2H), 2.35 (m, 2H), 1.95 (m, 2H), 1.30 (m, 4H), 1.20 (s, 3H), 1.05 (s, 3H), 1.03 (d, 3H), 0.91 (d, 3H), 0.90 (s, 18H), 0.90 (t, 9H), 0.50 (q, 6H), 0.10 (s, 3H), 0.05 (s, 6H), 0.03 (s, 3H).

(11b)—Compound 46

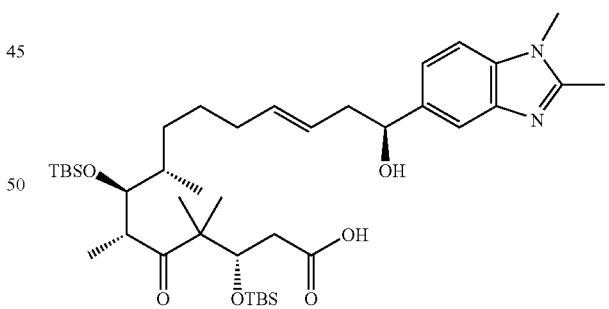

To a solution of 45 (50 mg, 0.067 mmol) in 2 mL i-PrOH/$H_2O$—4/1 is added LiOH (5 mg, 0.201 mmol) and the mixture is heated 6 h at 50° C. (in). After cooling to rt, the solution is quenched with a saturated solution of $NH_4Cl$, extracted twice with 10 mL $CH_2Cl_2$ and twice with 10 mL $Et_2O$. The combined organic layers are dried ($MgSO_4$) and concentrated in vacuum. Purification by flash column chromatography (Hexane/Acetone—50/50 to 0/100) afforded 46 as an colourless oil.

ESI-MS: $M(C_{40}H_{70}N_2O_6Si_2)$=731.2, $(M+H)^+$=731.4.

Rf: Hexane/Acetone—50/50: 0.46.

¹H NMR (400 MHz, CDCl₃): δ=7.60 (s, 1H), 7.30 (m, 2H), 5.45 (m, 1H), 5.35 (m, 1H), 4.80 (m, 1H), 4.40 (m, 1H), 3.80 (m, 1H), 3.74 (s, 3H), 3.20 (m, 1H), 2.65 (s, 3H), 2.45 (m, 2H), 2.35 (m, 2H), 1.98 (m, 2H), 1.40 (m, 4H), 1.20 (s, 3H), 1.10 (s, 3H), 1.05 (d, 3H), 0.95 (d, 3H), 0.94 (s, 18H), 0.09 (s, 3H), 0.07 (s, 3H), 0.04 (s, 3H), 0.02 (s, 3H).

(11c)—Compound 47: (E)-(4S,7R,8S,9S,16S)-4,8-Bis-(tert-butyl-dimethyl-silanyloxy)-16-(1,2-dimethyl-1H-benzoimidazol-5-yl)-5,5,7,9-tetramethyl-oxacyclohexadec-13-ene-2,6-dione

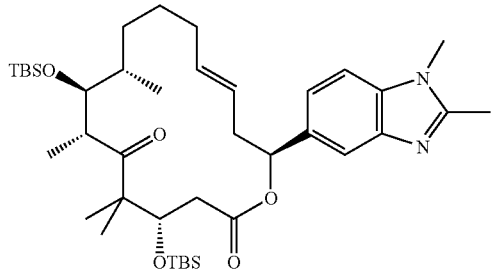

To a solution of 46 (345 mg, 0.471 mmol) in 12 mL THF at 0° C. is added triethylamine (0.395 mL, 2.831 mmol) followed by trichlorobenzylchloride (0.37 mL, 2.359 mmol). After stirring for 20 min at rt, the solution is diluted with 20 mL dry toluene and the resulting solution is added slowly in 2 h to a previously prepared solution of DMAP (0.575 g, 4.718 mmol) in 300 mL toluene. The reaction mixture is stirred at rt for 30 min and then concentrated in vacuum. The crude product is purified by flash column chromatography (Hexane/Acetone—90/10 to 70/30) to afford 47 as colourless oil.

ESI-MS: M(C₄₀H₆₈N₂O₅Si₂)=713.2, (M)⁺=713.4.
Rf: Hexane/Acetone—30/70: 0.56.
¹H NMR (400 MHz, CDCl₃): δ=7.62 (s, 1H), 7.26 (m, 2H), 5.87 (m, 1H), 5.52 (m, 1H), 5.37 (m, 1H), 4.40 (m, 1H), 3.97 (m, 1H), 3.70 (s, 3H), 3.17 (m, 1H), 2.60 (s, 3H), 2.60 (m, 2H), 2.55 (m, 2H), 1.92 (m, 2H), 1.45 (m, 4H), 1.20 (s, 3H), 1.10 (s, 3H), 1.05 (d, 3H), 0.95 (d, 3H), 0.94 (s, 9H), 0.84 (s, 9H), 0.11 (s, 3H), 0.09 (s, 3H), 0.04 (s, 3H), 0.01 (s, 3H).

Example 12

(1S,3S,7S,10R,11S,12S,16S)-3-(1,2-Dimethyl-1H-benzoimidazol-5-yl)-7,11-dihydroxy-8,8,10,12-tetramethyl-4,17-dioxa-bicyclo[14.1.0]heptadecane-5,9-dione (49)

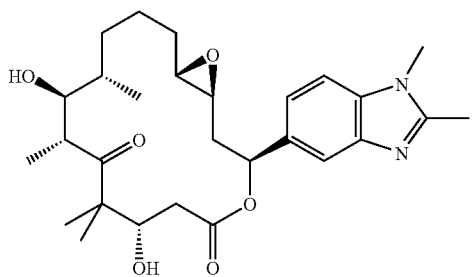

To a solution of 48 (24 mg, 0.0495 mmol) in 0.75 mL CH₃CN/DMM—1/1 at rt were added successively 0.46 mL of a buffer solution (Na₂B₄O₇.10 H₂O [0.05M] in Na₂EDTA [4.10⁻⁴M]), Bu₄N(HSO₄) (0.67 mg, 0.0019 mmol) and fructose-derived ketone (10.2 mg, 0.0396 mmol). The reaction mixture is cooled to 0° C. and were added separately, in a same time over 1 h30, Oxone® (42.6 mg, 0.089 mmol) in 0.6 mL Na₂EDTA and K₂CO₃ (39.7 mg, 0.287 mmol) in 0.6 mL H₂O. The solution is stirred 1 h30 at 0° C. and then is quenched with H₂O, extracted 3 times with 10 mL AcOEt. The combined organic layers are dried (MgSO₄) and concentrated in vacuum. Purification by flash column chromatography (Hexane/Acetone/MeOH—50/45/5) afforded 49 in a 8/1 ratio as white crystals.

ESI-MS: M(C₂₈H₄₀N₂O₆)=500.6, (M+H)⁺=501.2.
Rf: Hexane/Acetone—30/70: 0.17.
¹H NMR (400 MHz, CD₃OD): δ=7.62 (s, 1H), 7.41 (d, 1H), 7.35 (d, 1H), 6.05 (dd, 1H), 4.23 (dd, 1H), 3.88 (s, 3H), 3.72 (dd, 1H), 3.45 (m, 1H), 2.68 (m, 2H), 2.60 (s, 3H), 2.49 (m, 2H), 2.20 (m, 1H), 2.00 (m, 1H), 1.90 (m, 2H), 1.40 (m, 2H), 1.30 (s, 3H), 1.20 (d, 3H), 1.02 (s, 3H), 1.00 (d, 3H).

Example 13

(3E,13E)-(7R,8S,9S,16S)-16-(1,2-Dimethyl-1H-benzoimidazol-5-yl)-8-hydroxy-5,5,7,9-tetramethyl-oxacyclohexadeca-3,13-diene-2,6-dione (55)

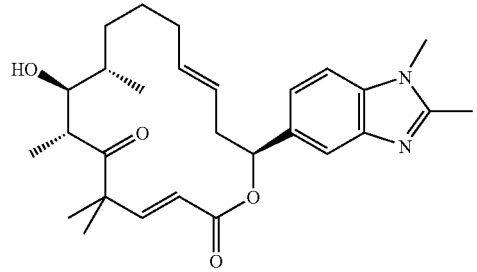

To a solution of 54 (12 mg, 0.0206 mmol) in 1 mL CH₃CN and in a Teflon tube is added at rt 0.2 mL of HF.Pyridine (70/30) and the reaction mixture is stirred 6 h at rt. The reaction mixture is washed with a 5% solution of NaHCO₃, extracted 3 times with 10 mL AcOEt and then the organic layers are dried (MgSO₄). Purification by flash column chromatography (CH₂Cl₂/MeOH—98/2) afforded 55 as white crystals.

ESI-MS: M(C₂₈H₃₈N₂O₄)=466.6, (M+H)⁺=467.1.
Rf: Hexane/Acetone—50/50: 0.18.
¹H NMR (400 MHz, CDCl₃): δ=7.71 (s, 1H), 7.20 (s, 2H), 6.91 (d, 1H), 6.15 (m, 1H), 6.01 (d, 1H), 5.45 (m, 2H), 3.70 (s, 3H), 3.60 (m, 1H), 3.18 (m, 1H), 2.60 (s, 3H), 2.17 (m, 2H), 1.97 (m, 2H), 1.60 (m, 2H), 1.40 (m, 2H), 1.34 (s, 3H), 1.18 (s, 3H), 1.15 (d, 3H), 0.95 (d, 3H).

(13a)—Compound 50

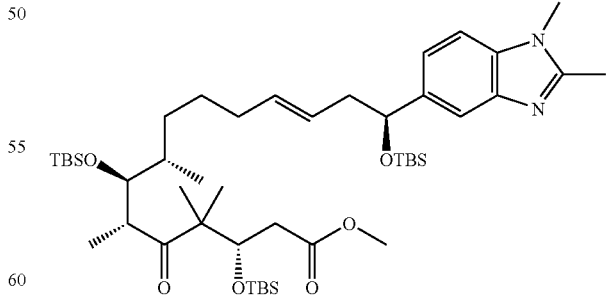

To a 0.5M solution of 9-BBN in 3 mL THF (2.2 mL, 1.095 mmol) is added dropwise 39 (0.28 g, 0.526 mmol) in 2 mL THF at rt. After 2 h TLC analysis revealed the complete consumption of the starting olefin. In a separate flask, containing 31 (0.2 g, 0.438 mmol) in 3 mL DMF were added successively, Cs₂CO₃ (0.28 g, 0.876 mmol), AsPh₃ (27 mg, 0.087 mmol), Pd(dppf)$_2$Cl$_2$ (64 mg, 0.087 mmol) and H$_2$O (0.24 mL, 13.143 mmol). In first solution is added H$_2$O (80 µL, 4.381 mmol) to quench the excess 9-BBN and the alkyl borane solution is added rapidly by syringe to the solution containing 31. The reaction mixture is stirred overnight at rt and quenched with H$_2$O, extracted 3 times with 25 mL Et$_2$O. The combined organic layers are dried (MgSO$_4$) and concentrated in vacuum. Purification by flash column chromatography (CH$_2$Cl$_2$-100 then Hexane/Acetone—70/30) afforded 50.

ESI-MS: M(C$_{47}$H$_{86}$N$_2$O$_6$Si$_3$)=859.4, (M+)$^+$=899.1.
Rf: Hexane/Acetone—50/50: 0.70.
$^1$H NMR (400 MHz, CDCl$_3$): δ=7.63 (s, 1H), 7.28 (m, 2H), 5.40 (m, 2H), 4.75 (m, 1H), 4.40 (m, 1H), 3.80 (s, 3H), 3.79 (m, 1H), 3.62 (s, 3H), 3.17 (m, 1H), 2.70 (s, 3H), 2.40 (m, 2H), 2.35 (m, 2H), 1.95 (m, 2H), 1.80 (m, 2H), 1.50 (m, 2H), 1.20 (s, 3H), 1.10 (s, 3H), 1.07 (d, 3H), 0.91 (s, 9H), 0.90 (d, 3H), 0.88 (s, 18H), 0.10 (s, 3H), 0.05 (s, 6H), 0.03 (s, 6H), −0.18 (s, 3H).

(13b)—Compound 51

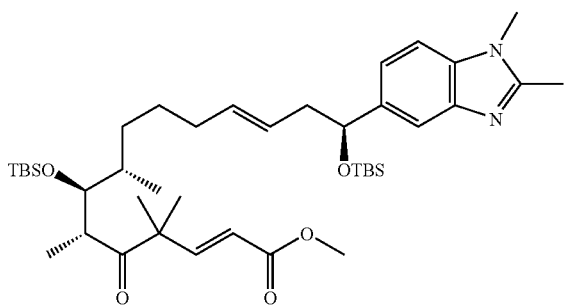

To a solution of 50 (250 mg, 0.291 mmol) in 6 mL THF under argon is added a 1M solution of TBAF (0.87 mL, 0.873 mmol) and the reaction mixture is stirred 8 h at rt. The solution is washed with a 5% solution of NaHCO$_3$ and extracted 3 times with 25 mL Et$_2$O. The combined organic layers are dried (MgSO$_4$) and concentrated in vacuum. Purification by flash column chromatography (Hexane/Acetone—90/10 to 50/50) afforded 51 as a colourless oil.

ESI-MS: M(C$_{41}$H$_{70}$N$_2$O$_5$Si$_2$)=727.2, (M+H)$^+$=729.3.
Rf: Hexane/Acetone—50/50: 0.46.
$^1$H NMR (400 MHz, CDCl$_3$): δ=7.60 (s, 1H), 7.21 (m, 2H), 7.06 (d, 1H), 5.90 (d, 1H), 5.40 (m, 2H), 4.72 (m, 1H), 3.80 (m, 1H), 3.76 (s, 3H), 3.73 (s, 3H), 3.05 (m, 1H), 2.60 (s, 3H), 2.40 (m, 2H), 1.92 (m, 2H), 1.30 (m, 2H), 1.29 (s, 3H), 1.28 (s, 3H), 1.05 (d, 3H), 0.89 (s, 9H), 0.88 (d, 3H), 0.88 (s, 9H), 0.05 (s, 3H), 0.04 (s, 6H), 0.02 (s, 6H), −0.18 (s, 3H).

(13c)—Compound 52

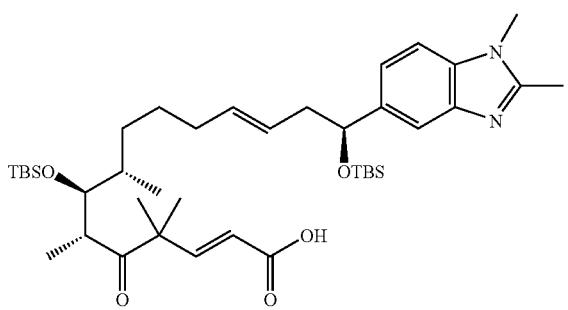

To a solution of 51 (50 mg, 0.0687 mmol) in 2 mL THF/H$_2$O—7/1 is added LiOH (10 mg, 0.412 mmol) and the mixture is stirred 25 h at rt. The solution is quenched with a 2% solution of KHSO$_4$ (until pH-5) extracted 3 times with 10 mL AcOEt. The combined organic layers are dried (MgSO$_4$) and concentrated in vacuum. Purification by flash column chromatography (Hexane/Acetone—90/10 to 50/50) afforded 52 as colourless oil.

ESI-MS: M(C$_{40}$H$_{68}$N$_2$O$_5$Si$_2$)=713.1, (M+H)$^+$=713.3.
Rf: Hexane/Acetone—50/50: 0.37.
$^1$H NMR (400 MHz, CD$_3$OD): δ=7.58 (s, 1H), 7.52 (d, 1H), 7.38 (d, 1H), 7.04 (d, 1H), 5.90 (d, 1H), 5.40 (m, 2H), 4.82 (m, 1H), 3.81 (s, 3H), 3.80 (m, 1H), 3.05 (m, 1H), 2.63 (s, 3H), 2.40 (m, 2H), 1.92 (m, 2H), 1.30 (m, 2H), 1.29 (s, 3H), 1.25 (s, 3H), 1.05 (d, 3H), 0.89 (s, 9H), 0.88 (d, 3H), 0.88 (s, 9H), 0.05 (s, 6H), 0.04 (s, 3H), −0.16 (s, 3H).

(13d)—Compound 53

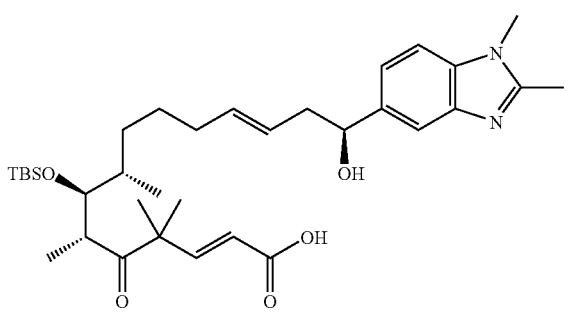

To a solution of 52 (30 mg, 0.042 mmol) in 2 mL THF under argon is added a 1M solution of TBAF (0.25 mL, 0.252 mmol) and the reaction mixture is stirred 24 h at rt. The solution is washed with a 5% solution of NaHCO$_3$ and extracted 3 times with 25 mL AcOEt. The combined organic layers are dried (MgSO$_4$) and concentrated in vacuum. Purification by flash column chromatography (CH$_2$Cl$_2$/MeOH—95/5) afforded 53, as an oil.

ESI-MS: M(C$_{34}$H$_{54}$N$_2$O$_5$Si)=598.9, (M+H)$^+$=599.2.
Rf: CH$_2$Cl$_2$/MeOH—90/10: 0.29.
$^1$H NMR (400 MHz, CD$_3$OD): δ=7.58 (s, 1H), 7.41 (d, 1H), 7.28 (d, 1H), 6.95 (d, 1H), 5.91 (d, 1H), 5.40 (m, 2H), 4.75 (m, 1H), 3.80 (s, 3H), 3.80 (m, 1H), 3.15 (m, 1H), 2.60 (s, 3H), 2.45 (m, 2H), 1.92 (m, 2H), 1.40 (m, 2H), 1.27 (s, 3H), 1.24 (s, 3H), 1.03 (d, 3H), 0.89 (s, 9H), 0.85 (d, 3H), 0.05 (s, 6H).

(13e)—Compound 54: (3E,13E)-(7R,8S,9S,16S)-8-(tert-Butyl-dimethyl-silanyloxy)-16-(1,2-dimethyl-1H-benzoimidazol-5-yl)-5,5,7,9-tetramethyl-oxacyclohexadeca-3,13-diene-2,6-dione

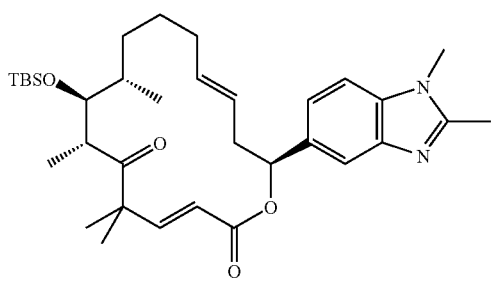

To a solution of 53 (20 mg, 0.033 mmol) in 2 mL THF at 0° C. is added triethylamine (28 JAL, 0.20 mmol) followed by trichlorobenzylchloride (26 µL, 0.167 mmol). After stirring for 20 min at rt, the solution is diluted with 5 mL dry toluene and the resulting solution is added slowly in 1 h to a previously prepared solution of DMAP (41 mg, 0.334 mmol) in 20 mL toluene. The reaction mixture is stirred at rt for 30 min and then concentrated in vacuum. The crude product is purified by flash column chromatography (CH$_2$Cl$_2$/MeOH—98/2) to afford 54 as white crystals.

ESI-MS: M(C$_{34}$H$_{52}$N$_2$O$_4$Si)=580.9, (M+H)$^+$=581.2.

Rf: Hexane/Acetone—50/50: 0.37.

$^1$H NMR (400 MHz, CDCl$_3$): δ=7.71 (s, 1H), 7.25 (s, 2H), 6.88 (d, 1H), 6.20 (m, 1H), 6.05 (d, 1H), 5.50 (m, 2H), 3.70 (s, 3H), 3.70 (m, 1H), 3.08 (m, 1H), 2.60 (s, 3H), 2.18 (m, 2H), 1.98 (m, 2H), 1.60 (m, 2H), 1.40 (m, 2H), 1.29 (s, 3H), 1.20 (s, 3H), 1.10 (d, 3H), 0.95 (d, 3H), 0.84 (s, 9H), 0.05 (s, 3H), 0.04 (s, 3H).

Example 14

(E)-(1S,3S,10R,11S,12S,16S)-3-(1,2-Dimethyl-1H-benzoimidazol-5-yl)-11-hydroxy-8,8,10,12-tetramethyl-4,17-dioxa-bicyclo[14.1.0]heptadec-6-ene-5,9-dione (56)

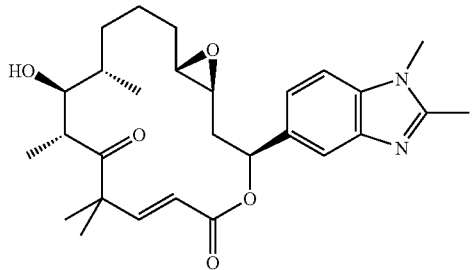

To a solution of 55 (40 mg, 0.0857 mmol) in 1.3 mL CH$_3$CN/DMM—1/1 at rt were added successively 0.8 mL of a buffer solution (Na$_2$B$_4$O$_7$.10 H$_2$O [0.05M] in Na$_2$EDTA [4.10$^{-4}$M]), BU$_4$N(HSO$_4$) (1.2 mg, 0.003 mmol) and fructose-derived ketone (17.7 mg, 0.0685 mmol). The reaction mixture is cooled to 0° C. and were added separately, in a same time over 1 h30, Oxone® (73.8 mg, 0.120 mmol) in 1 mL Na$_2$EDTA and K$_2$CO$_3$ (68.7 mg, 0.497 mmol) in 1 mL H$_2$O. The solution is stirred 3 h at 0° C. and then is quenched with H$_2$O, extracted 3 times with 10 mL AcOEt. The combined organic layers are dried (MgSO$_4$) and concentrated in vacuum. Purification of crude product by prep-HPLC afforded 56, 50% conversion in a 8/1 ratio.

ESI-MS: M(C$_{28}$H$_{38}$N$_2$O$_5$)=482.6, (M+H)$^+$=483.2.

Rf: Hexane/Acetone—30/70: 0.23.

$^1$H NMR (400 MHz, CDCl$_3$): δ=7.72 (s, 1H), 7.27 (s, 2H), 6.91 (d, 1H), 6.37 (d, 1H), 6.05 (d, 1H), 3.80 (m, 1H), 3.77 (s, 3H), 3.19 (m, 1H), 2.90 (m, 2H), 2.61 (s, 3H), 2.58 (m, 2H), 1.97 (m, 4H), 1.60 (m, 2H), 1.40 (m, 2H), 1.43 (s, 3H), 1.20 (s, 3H), 1.18 (d, 3H), 1.01 (d, 3H).

Example 15

3-(1,2-Dimethyl-1H-benzoimidazol-5-yl)-7,11-dihydroxy-8,8,10,12-tetramethyl-4-oxa-bicyclo[14.1.0]heptadecane-5,9-dione (Compound 64)

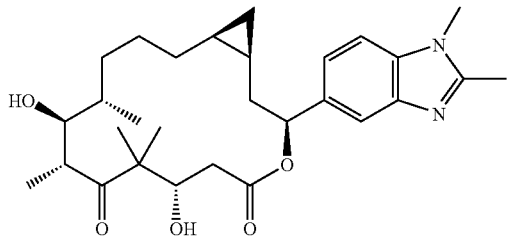

To a 50 ml plastic tube, equipped with a magnetic stir bar, are successively added 63 (60 mg), 5 ml of acetonitrile. To this solution is rapidly added HF-Pyridine complex (1 ml). The reaction is monitored by TLC (CH$_2$Cl$_2$/MeOH: 95/5) and the mixture is stirred at room temperature for 5 h. The reaction mixture is then carefully added dropwise to an Erlenmeyer containing methylene chloride (30 ml), distilled water (30 ml) and sodium bicarbonate (5 g).

The two layers are separated by decantation and the aqueous phase is extracted three times with methylene chloride (20 ml). After drying with magnesium sulfate, the solvents are removed under vacuo and the crude mixture is purified by flash chromatography (CH$_2$Cl$_2$/MeOH: 95/5) followed by preparative HPLC to finally give the pure diastereoisomer 64, as a white powder.

ESI-MS: 499.1 (M+H)$^+$.

HPLC: Rt=7.02 min (method 1).

Rf=0.25 (CH$_2$Cl$_2$/MeOH: 95/5)

$^1$H-NMR (400 MHz, DMSO-d6/ppm): 7.50 (s, 1H), 7.37 (d, 8 Hz, 1H), 7.29 (d, 8 Hz, 1H), 5.75 (dd, 3.9 Hz, 1H), 5.08 (d, 6 Hz, 1Hz, 4.42 (d, 6 Hz, 1H), 3.95 (m, 1H), 3.69 (s, 3H), 3.53 (m, 1H), 3.12 (m, 1H), 2.55-2.30 (m, 2H), 2.50 (s, 3H), 2.03 (A of ABX, 1H), 1.75 (B of ABX, 1H), 1.52-1.13 (m, 7H), 1.21 (s, 3H), 1.05 (d, 6 Hz, 3H), 0.95 (s, 3H), 0.93 (d, 3H), 0.90 (m, 1H), 0.70 (m, 1H), 0.57 (m, 1H), −0.32 (m, 1H).

(15a)-Compound 58

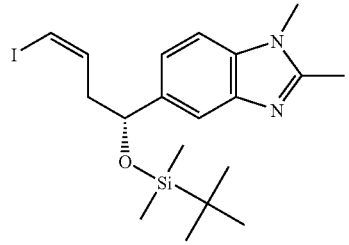

Sodium bis(trimethylsilyl)-amide (3.6 ml of a 1M THF solution) is slowly added at room temperature to a suspension of the finely crushed iodomethyl-triphenylphosphonium iodide salt (2.0 g) in 10 ml THF. The solution becomes quickly orange. After the end of the addition (~10 min), the mixture is cooled down to −78° C. and the aldehyde 57 (1.0 g) in of THF (5 ml) is added dropwise. After 60 min stirring at −78° C., the reaction is quenched by the addition of a saturated solution of Ammonium chloride (20 ml) under vigorous stirring. The mixture is then allowed to warm up to room temperature and CH$_2$Cl$_2$ is added (50 ml). The two layers are separated by decantation and the aqueous phase is extracted twice with CH$_2$Cl$_2$ (20 ml). After drying of the joined organic phases with magnesium sulfate and evaporation of the solvents under vacuo, the residue is taken in hexane (20 ml) in order to precipitate the triphenylphosphine oxide. The precipitate is filtered off and washed with hexane (2 ml) and the filtrate is kept at 4° C. overnight to complete the precipitation of the triphenylphosphine oxide. The solvent is removed under vacuo and the crude is purified by Flash chromatography (EtOAc) to yield 58 as a clear oil.

ESI-MS: 456.9 (M+H)$^+$.

Rf=0.54 (CH$_2$Cl$_2$/MeOH: 90/10).

¹H-NMR (400 MHz, CDCl₃/ppm): 7.75 (s, 1H), 7.23 (m, 2H), 6.22 (m, 2H), 4.91 (m, 1H), 3.74 (s, 3H), 2.67-2.49 (m, 2H), 2.63 (s, 3H), 0.90 (s, 9H), 0.05 (s, 3H), −0.10 (s, 3H).

(15b)-Compound 59

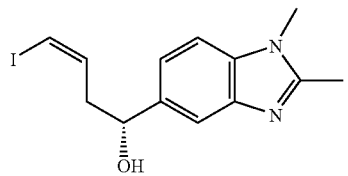

Camphorsulfonic acid (1.87 g) is added carefully (~10 installments) in a solution of 58 (914 mg) in CH₂Cl₂ (50 ml) and methanol (50 ml) at 0° C. The mixture is then allowed to warm up to room temperature and is stirred for 17 h. The mixture is then carefully poured in an Erlenmeyer containing distilled water (150 ml) and sodium bicarbonate (1.34 g) under vigorous stirring. The layers are separated and the aqueous phase is extracted three times with CH₂Cl₂ (50 ml). The organic phases are joined, dried over sodium sulfate and the solvents are removed under vacuo. The crude is purified by flash chromatography (CH₂Cl₂/MeOH: 95/5) in order to give 59, a white solid.

ESI-MS: 343.0 (M+H)⁺.

Rf=0.35 (CH₂Cl₂/MeOH: 90/10).

¹H-NMR (400 MHz, CDCl₃/ppm): 7.66 (s, 1H), 7.29 (m, 2H), 6.29 (m, 2H), 4.97 (m, 1H), 3.75 (s, 3H), 2.78-2.62 (m, 2H), 2.62 (s, 3H).

(15c)—Compound 60

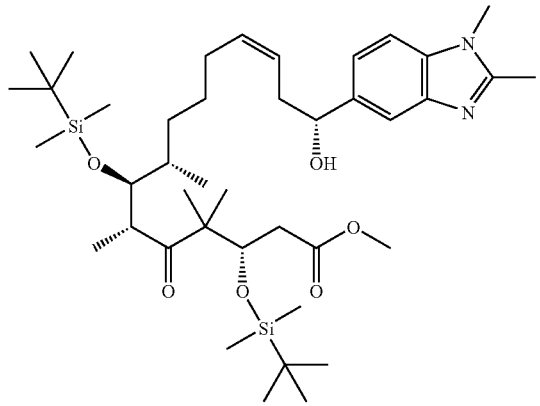

Flask A: To a solution of 39 (1.16 g) in 20 ml THF is added 9-BBN (8.8 ml of a 0.5M solution in THF) drop wise at 0° C. After the end of the addition, the ice bath is removed and the reaction mixture is allowed to warm up to room temperature. The reaction is monitored by TLC and is complete after 120 minutes. The excess of 9-BBN is quenched by addition of 200 μl of distilled water.

Flask B: In a 100 ml three-necked round bottomed flask, are successively added the vinyl iodide 59 (600 mg) and 20 ml of DMF. The solution is cooled down to 0° C. and Cesium carbonate (1.19 g), triphenylarsine (107 mg), the Palladium catalyst (297 mg) and distilled water (880 μl) are successively added. The content of Flask A is then rapidly added (30 sec) under vigorous stirring. After 10 minutes at 0° C., the ice bath is removed and the reaction mixture is allowed to warm up to room temperature. The reaction is monitored by MS and is complete after. The mixture is then poured in an Erlenmeyer containing 300 ml of diethyl ether and 300 ml of a saturated aqueous ammonium chloride. The two layers are separated by decantation and the aqueous phase is extracted twice with 200 ml of diethyl ether. The organic phases are joined and dried with magnesium sulfate. Evaporation of the solvents under vacuo yielded a brown oil which is purified by flash chromatography (Hexanes/Acetone: 80/20 to 60/40) to finally yield 60 as a thick yellow oil.

ESI-MS: 745.2 (M+H)⁺.

Rf=0.45 (CH₂Cl₂/MeOH: 90/10).

¹H-NMR (400 MHz, CDCl₃/ppm): 7.64 (s, 1H), 7.26 (m, 2H), 5.53 (m, 1H), 5.40 (m, 1H), 4.83 (m, 1H), 4.40 (dd, 1H), 3.77 (dd, 1H), 3.73 (s, 3H), 3.68 (s, 3H), 3.14 (m, 1H), 2.71-2.48 (m, 2H), 2.63 (s, 3H), 2.45 (A of ABX, 1H), 2.29 (B of ABX, 1H), 2.05 (m, 2H), 1.46-1.0 (m, 5H), 1.25 (s, 3H), 1.08 (s, 3H), 1.05 (d, 7Hz, 3H), 0.92 (s, 9H), 0.89 (d, 3H), 0.88 (s, 9H), 0.10 (s, 3H), 0.06 (s, 6H), 0.02 (s, 3H).

(15d)—Compound 61

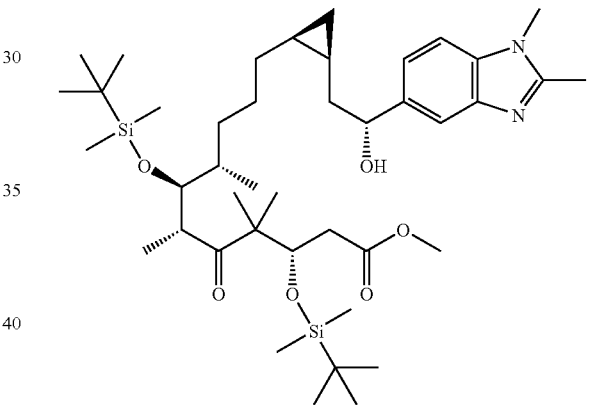

To a solution of Et₂Zn (3 ml of a 1.0M solution in hexane) in CH₂Cl₂ (6 ml), is slowly added (15 min), at −10° C., a solution of TFA (228 μl) in CH₂Cl₂ (3 ml). The reaction mixture is stirred for another 15 minutes and a solution of diiodomethane (240 μl) in CH₂Cl₂ (3 ml) is added. After stirring for 30 minutes, 60 (250 mg) in CH₂Cl₂ (3 ml) is added drop wise and the mixture is stirred at −10° C. for another 30 minutes. The reaction is then quenched by addition of a aqueous saturated ammonium chloride solution (15 ml). The two layers are separated by decantation and the aqueous phase is extracted three times with CH₂Cl₂. The organic phases are joined, dried over MgSO₄ and the solvents are evaporated. The crude is then purified by flash chromatography (CH₂Cl₂/MeOH: 95/5) to give 61, as a white foam.

ESI-MS: 759.3 (M+H)⁺.

Rf=0.45 (CH₂Cl₂/MeOH: 90/10).

¹H-NMR (400 MHz, C₆D₆/ppm): 8.04 (s, 1H), 7.43 (d, 5 Hz, 1H), 6.91 (d, 5 Hz, 1H), 4.89 (m, 1H), 4.63 (dd, 1H), 3.98 (dd, 1H), 3.33 (s, 3H), 3.19 (m, 1H), 2.62 (s, 3H), 2.58 (A of ABX, 1H), 2.31 (B of ABX, 1H), 2.10-2.0 (m, 1H), 2.05 (s, 3H), 1.78 (m, 1H), 1.62-1.0 (m, 9H), 1.14 (d, 7Hz, 3H), 1.12 (s, 3H), 1.11 (s, 3H), 1.04 (s, 9H), 1.02 (d, 3H), 0.96 (s, 9H), 0.81 (m, 1H), 0.62 (m, 2H), 0.17 (s, 3H), 0.15 (s, 3H), 0.14 (s, 3H), 0.12 (s, 3H), −0.15 (m, 1H).

(15e)—Compound 62

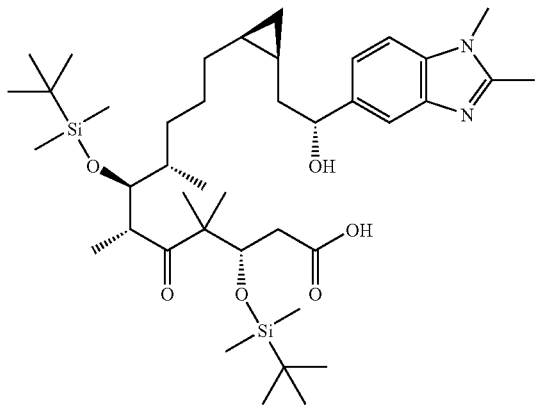

Lithium hydroxide (77 mg) is added to a solution of 61 (400 mg) in a mixture of isopropanol (12 ml) and water (3 ml). The reaction mixture is then warmed up to 60° C. and stirred for 2 h. The mixture is then poured into an Erlenmeyer containing 30 ml of $CH_2Cl_2$ and 30 ml of water. The mixture is then acidified to pH 5 by a slow addition of Hydrochloric acid 1M under vigorous stirring (pH meter). The two layers are separated by decantation and the aqueous phase is extracted three times with 30 ml of $CH_2Cl_2$. The organic phases are joined and after drying with magnesium sulfate, removing of the solvents under vacuo, the crude is purified by flash chromatography ($CH_2Cl_2$/Methanol: 90/10) to yield 62, as a white foam.

ESI-MS: 745.2 (M+H)$^+$.

Rf=0.22 ($CH_2Cl_2$/MeOH: 94/6).

$^1$H-NMR (400 MHz, CD$_3$OD/ppm): 7.57 (s, 1H), 7.42 (A of AB, 1H), 7.32 (B of AB, 1H), 4.74 (m, 1H), 4.34 (m, 1H), 3.80 (s, 3H), 3.75 (m, 1H), 3.22 (m, 1H), 2.63 (bs, 3H), 2.45 (A of ABX, 1H), 2.18 (B of ABX, 1H), 1.81 (m, 1H), 1.66 (m, 1H), 1.53-0.78 (m, 19H), 0.92 (s, 9H), 0.84 (s, 9H), 0.78-0.59 (m, 3H), 0.08 (s, 3H), 0.07 (s, 6H), 0.02 (bs, 3H), −0.16 (m, 1H).

(15f)—Compound 63

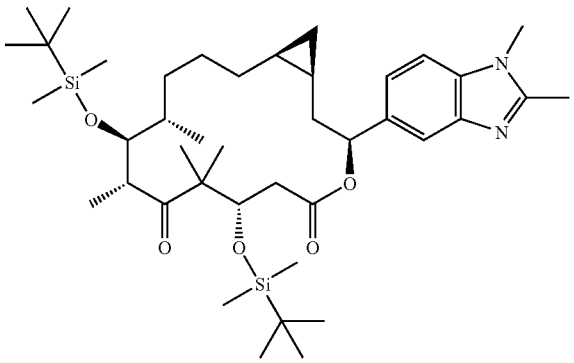

To a solution of 62 (160 mg) and triphenylphosphine (207 mg) in toluene (30 ml) is slowly added, at −13° C. (ice/ethanol bath) over a period of one hour, a solution of DIAD (105 μl). The reaction is quenched by addition of MeOH (3 ml) and the solvents are evaporated under vacuo. The crude mixture is then purified by flash chromatography (hexane/acetone: 70/30 to 50/50 with 1% of Et$_3$N) to yield 63, as a white foam.

ESI-MS: 727.2 (M+H)$^+$.

Rf=0.45 (Hex/acetone: 50/50).

$^1$H-NMR (400 MHz, CDCl$_3$/ppm): 7.63 (s, 1H), 7.24 (m, 2H), 5.72 (dd, 3.7 Hz, 1H), 3.99 (m, 1H), 3.89 (d, 7 Hz, 1H), 3.71 (s, 3H), 3.02 (m, 1H), 2.80-2.51 (m, 2H), 2.59 (s, 3H), 2.17 (m, 1H), 1.78-0.74 (m, 9H), 1.27 (s, 3H), 1.13 (s, 3H), 1.09 (d, 7Hz, 3H), 1.0 (d, 7 Hz, 3H), 0.97 (s, 9H), 0.89 (s, 9H), 0.71-0.58 (m, 3H), 0.13 (s, 6H), 0.09 (s, 3H), 0.04 (s, 3H), −0.32 (m, 1H).

Example 16

(1S,3S,7S,10R,11S,12S,16R)-3-(1,2-Dimethyl-1H-benzoimidazol-5-yl)-7,11-dihydroxy-8,8,10,12-tetramethyl-4-oxa-bicyclo[14.1.0]heptadecane-5,9-dione (73)

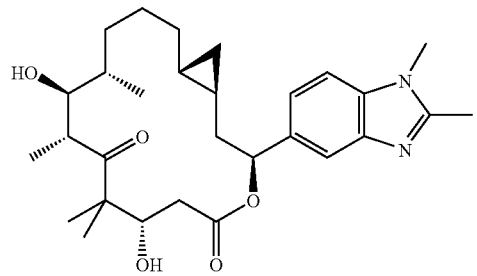

To a solution of 72 (70 mg, 0.096 mmol) in 4 mL CH$_3$CN and in a Teflon tube is added at rt 1 mL of HF.Pyridine (70/30) and the reaction mixture is stirred 2 h at rt. The reaction mixture is washed with a 5% solution of NaHCO$_3$ (pH-5), extracted 3 times with 15 mL AcOEt and then the organic layers are dried (MgSO$_4$). Crude product is purified by prep-HPLC to afford pure 73 as white crystals.

ESI-MS: M(C$_{29}$H$_{42}$N$_2$O$_5$)=498.6, (M+H)$^+$=499.2.

Rf: Hexane/Acetone—50/50: 0.19.

$^1$H NMR (400 MHz, CD$_3$OD): δ=7.60 (s, 1H), 7.38 (m, 1H), 7.28 (m, 1H), 5.97 (m, 1H), 4.30 (m, 1H), 3.92 (m, 1H), 3.70 (s, 3H), 3.30 (m, 1H), 2.60 (s, 3H), 2.42 (m, 1H), 2.10 (m, 1H), 1.60 (m, 2H), 1.40 (m, 1H), 1.37 (s, 3H), 1.20 (d, 3H), 1.01 (s, 3H), 0.99 (d, 3H), 0.80 (m, 1H), 0.60 (m, 1H), 0.22 (m, 2H).

(16a)—Compound 65

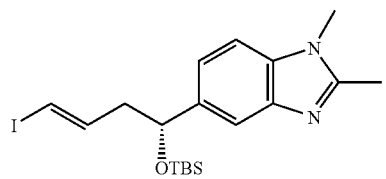

To a solution of CrCl$_2$ (3.0 g, 24.06 mmol) in 10 mL THF at rt, is added dropwise over 30 min a mixture of 57 (1.0 g, 3.0 mmol) and CHI$_3$ (2.4 g, 6.0 mmol) in 60 mL of Dioxane. The reaction mixture is stirred 3 h at rt and quenched with 20 mL H$_2$O, extracted 3 times with 20 mL Et$_2$O and 3 times with 20 mL AcOEt. The combined organic layers are dried (MgSO$_4$) and concentrated in vacuum. Purification by flash column chromatography (CH$_2$Cl$_2$/Acetone—100/0 to 50/50) afforded 65 in a 5/1 ratio as yellowish oil.

ESI-MS: M(C$_{19}$H$_{29}$N$_2$OSiI)=456.4, (M+H)$^+$=456.9.

Rf: Acetone—100: 0.50.

$^1$H NMR (400 MHz, CDCl$_3$): δ=7.58 (s, 1H), 7.20 (m, 2H), 6.52 (m, 1H), 6.00 (dt, 1H), 4.80 (m, 1H), 3.70 (s, 3H), 2.80 (s, 3H), 2.40 (m, 2H), 0.90 (s, 9H), 0.05 (s, 3H), −0.17 (s, 3H).

(16b)—Compound 66

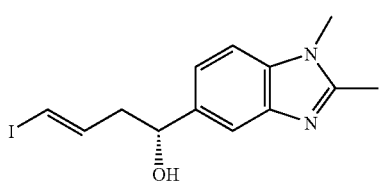

To a solution of 65 (0.74 g, 1.621 mmol) in 75 mL of a CH$_2$Cl$_2$/MeOH—1/1 solution, is added CSA (1.5 g, 6.485 mmol) and the reaction mixture is stirred 2 days at rt. The mixture is quenched with NaHCO$_3$ (5%) solution until pH-7 and extracted 3 times with 25 mL AcOEt. The combined organic layers are dried (MgSO$_4$) and concentrated in vacuum. Purification by flash column chromatography (CH$_2$Cl$_2$/MeOH—100/0 to 90/10) afforded 66. Crystallization in CH$_2$Cl$_2$/Hexane—1/1 with 3 drops of MeOH afforded pure diastereoisomer as white crystals.

ESI-MS: M(C$_{13}$H$_{15}$N$_2$OI)=342.1, (M+H)$^+$=342.9.

Rf: Hexane/Acetone—50/50: 0.25.

$^1$H NMR (400 MHz, CDCl$_3$): δ=7.61 (s, 1H), 7.22 (m, 2H), 6.55 (m, 1H), 6.15 (d, 1H), 4.85 (m, 1H), 3.73 (s, 3H), 2.61 (s, 3H), 2.55 (m, 2H).

(16c)—Compound 67

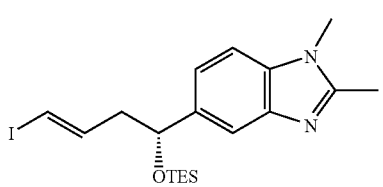

To a solution of 66 (0.28 g, 0.818 mmol) in 12 mL CH$_2$Cl$_2$ at 0° C. is added dropwise 2,6-lutidine (0.285 mL, 2.455 mmol) followed by TESOTf (0.37 mL, 1.636 mmol). The mixture is stirred 1 h at 0° C. and then is quenched with a saturated solution of NH$_4$Cl, extracted 3 times with 25 mL AcOEt. The combined organic layers are dried (MgSO$_4$) and concentrated in vacuum. Purification by flash column chromatography (Hexane/Acetone—80/20 to 50/50) afforded 67 as white crystals.

ESI-MS: M(C$_{19}$H$_{29}$N$_2$OSiI)=456.4, (M+H)$^+$=456.9.

Rf: Hexane/Acetone—50150: 0.67.

$^1$H NMR (400 MHz, CDCl$_3$): δ=7.58 (s, 1H), 7.20 (m, 2H), 6.50 (m, 1H), 6.00 (dt, 1H), 4.80 (m, 1H), 3.70 (s, 3H), 2.80 (s, 3H), 2.40 (m, 2H), 0.94 (t, 9H), 0.50 (q, 6H).

(16d)—Compound 68

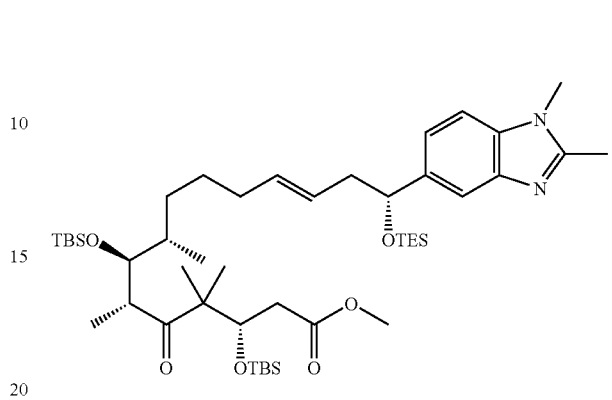

To a 0.5M solution of 9-BBN in 4 mL THF (3.3 mL, 1.643 mmol) is added dropwise 39 (0.417 g, 0.657 mmol) in 5 mL THF at rt. After 2 h TLC analysis revealed the complete consumption of the starting olefin. In a separate flask, containing 67 (0.3 g, 0.657 mmol) in 10 mL DMF were added successively, Cs$_2$CO$_3$ (0.428 g, 1.314 mmol), AsPh$_3$ (40 mg, 0.131 mmol), Pd(dppf)$_2$Cl$_2$ (96 mg, 0.131 mmol) and H$_2$O (0.355 mL, 19.717 mmol). In first solution is added H$_2$O (118 μL, 6.572 mmol) to quench the excess 9-BBN and the alkyl borane solution is added rapidly by syringe to the solution containing 67. The reaction mixture is stirred 2 h at rt and quenched with H$_2$O, extracted 3 times with 25 mL AcOEt. The combined organic layers are dried (MgSO$_4$) and concentrated in vacuum. Purification by flash column chromatography (Hexane/Acetone—90/10 to 70/30) afforded 68 as colourless oil.

ESI-MS: M(C$_{47}$H$_{86}$N$_2$O$_6$Si$_3$)=859.5, (M+H)$^+$=859.2.

Rf: Hexane/Acetone—50/50: 0.73.

$^1$H NMR (400 MHz, CDCl$_3$): δ=7.60 (s, 1H), 7.20 (m, 2H), 5.40 (m, 2H), 4.73 (m, 1H), 4.40 (m, 1H), 3.78 (m, 1H), 3.71 (s, 3H), 3.67 (s, 3H), 3.17 (m, 1H), 2.60 (s, 3H), 2.40 (m, 2H), 2.35 (m, 2H), 1.95 (m, 2H), 1.30 (m, 4H), 1.20 (s, 3H), 1.05 (s, 3H), 1.03 (d, 3H), 0.91 (d, 3H), 0.90 (s, 18H), 0.90 (t, 9H), 0.50 (q, 6H), 0.12 (s, 3H), 0.05 (s, 6H), 0.03 (s, 3H).

(16e)—Compound 69

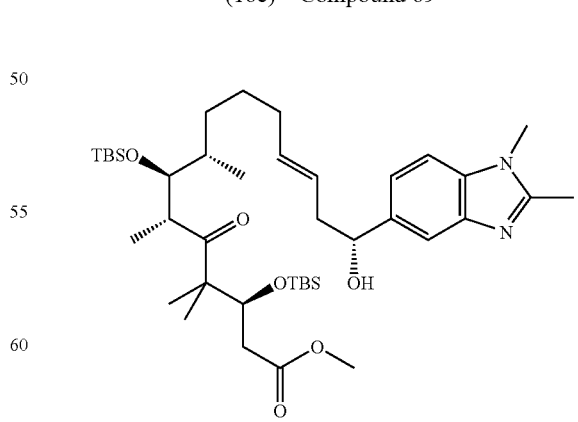

To a solution of 68 (0.325 g, 0.378 mmol) in 10 mL THF at rt is added a mixture TBAF/AcOH—1/1 (2.27 mL, 2.269 mmol) and the reaction is stirred 5 h at rt. The solvent is removed under vacuum and the crude product is purified by flash column chromatography (Hexane/Acetone/MeOH—50/45/5) to afford 69.

ESI-MS: $M(C_{41}H_{72}N_2O_6Si_2)$=745.2, $(M+H)^+$=745.2.
Rf: Hexane/Acetone—50/50: 0.52.
$^1$H NMR (400 MHz, CDCl$_3$): δ=7.62 (s, 1H), 7.22 (m, 2H), 5.58 (m, 1H), 5.41 (m, 1H), 4.80 (m, 1H), 4.40 (m, 1H), 3.78 (m, 1H), 3.71 (s, 3H), 3.62 (s, 3H), 3.17 (m, 1H), 2.60 (s, 3H), 2.45 (m, 2H), 2.30 (m, 2H), 2.00 (m, 2H), 1.40 (m, 4H), 1.21 (s, 3H), 1.07 (s, 3H), 1.05 (d, 3H), 0.92 (d, 3H), 0.91 (s, 18H), 0.11 (s, 3H), 0.05 (s, 6H), 0.02 (s, 3H).

(16f)—Compound 70

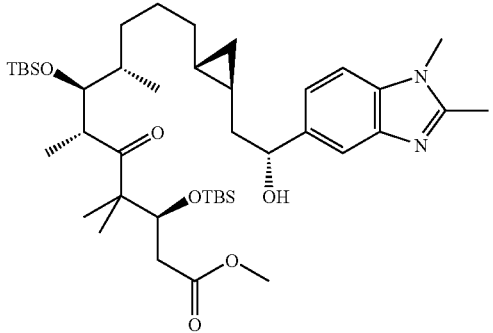

To a 1M solution of Et$_2$Zn (3.38 mL, 3.38 mmol) in 5 mL CH$_2$Cl$_2$ at −13° C., is added dropwise over 10 min TFA (0.259 mL, 3.38 mmol) in 2 mL CH$_2$Cl$_2$. The reaction mixture is stirred 15 min at −13° C. and then CH$_2$I$_2$ (0.273 mL, 3.38 mmol) in 2 mL CH$_2$Cl$_2$ is added dropwise. After 30 min at −13° C., 69 (0.28 g, 0.375 mmol) in 2 mL CH$_2$Cl$_2$ is added dropwise. The reaction mixture is stirred 20 min and then is quenched with a saturated solution of NH$_4$Cl extracted 3 times with 20 mL CH$_2$Cl$_2$. The combined organic layers are dried (MgSO$_4$) and concentrated in vacuum. Purification by flash column chromatography (Hexane/Acetone—50/50) afforded 70 as colourless oil.

ESI-MS: $M(C_{42}H_{74}N_2O_6Si_2)$=759.2, $(M+H)^+$=759.2.
Rf: Hexane/Acetone—50/50: 0.28.
$^1$H NMR (400 MHz, CD$_3$OD): δ=7.58 (s, 1H), 7.42 (d, 1H), 7.30 (d, 1H), 4.67 (m, 1H), 4.38 (m, 1H), 3.81 (s, 3H), 3.77 (m, 1H), 3.64 (s, 3H), 3.30 (m, 1H), 3.20 (m, 1H), 2.70 (s, 3H), 2.45 (m, 1H), 2.25 (m, 1H), 1.60 (m, 2H), 1.40 (m, 4H), 1.22 (s, 3H), 1.07 (s, 3H), 1.05 (d, 3H), 0.92 (d, 3H), 0.91 (s, 18H), 0.32 (m, 2H), 0.15 (s, 3H), 0.08 (s, 3H), 0.05 (s, 3H), 0.02 (s, 3H).

(16g)—Compound 71

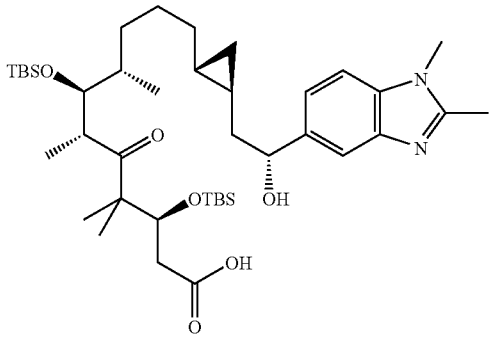

To a solution of 70 (0.22 g, 0.289 mmol) in 9 mL i-PrOH/H$_2$O—4/1 is added LiOH (42 mg, 1.738 mmol) and the mixture is heated 3 h at 60° C. (out). After cooling to rt, the solution is quenched with a 2% solution of KHSO$_4$ (pH-5) extracted twice with 10 mL CH$_2$Cl$_2$ and twice with 10 mL AcOEt. The combined organic layers are dried (MgSO$_4$) and concentrated in vacuum. Purification by flash column chromatography (Hexane/Acetone/MeOH—90/10/0 to 45/45/10) afforded 71 as an oil.

ESI-MS: $M(C_{41}H_{72}N_2O_6Si_2)$=745.2, $(M+H)^+$=745.2.
Rf: Hexane/Acetone—50/50: 0.23.
$^1$H NMR (400 MHz, CD$_3$OD): δ=7.58 (s, 1H), 7.42 (d, 1H), 7.30 (d, 1H), 4.79 (m, 1H), 4.38 (m, 1H), 3.80 (s, 3H), 3.76 (m, 1H), 3.74 (m, 1H), 3.20 (m, 1H), 2.60 (s, 3H), 2.41 (m, 1H), 2.20 (m, 1H), 1.98 (m, 2H), 1.40 (m, 4H), 1.21 (s, 3H), 1.10 (s, 3H), 1.05 (d, 3H), 0.94 (d, 3H), 0.94 (s, 9H), 0.93 (s, 9H), 0.28 (m, 2H), 0.10 (s, 3H), 0.07 (s, 3H), 0.04 (s, 3H), 0.02 (s, 3H).

(16h)—Compound 72: (1S,3S,7S,10R,11S,12S,16R)-7,11-Bis-(t-butyl-dimethyl-silanyloxy)-3-(1,2-dimethyl-1H-benzoimidazol-5-yl)-8,8,10,12-tetramethyl-4-oxa-bicyclo[14.1.0]heptadecane-5,9-dione

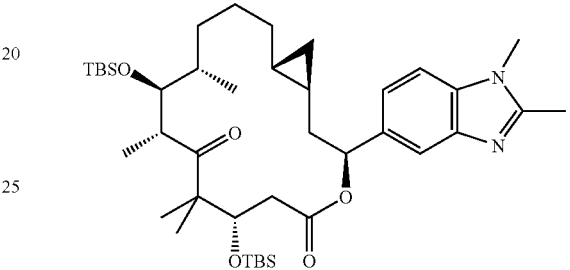

To a solution of 71 (0.1 g, 0.134 mmol) in 25 mL toluene at −10° C. is added PPH$_3$ (0.106 g, 0.402 mmol) followed by DIAD (52 µL, 0.268 mmol) in 8 mL toluene dropwise over 1 h30. The reaction mixture is quenched with a saturated NH$_4$Cl solution and extracted 3 times with 20 mL AcOEt. The combined organic layers are dried (MgSO$_4$) and concentrated in vacuum. Purification by flash column chromatography (Hexane/Acetone—50/50 to 0/100) afforded 72, 70% conversion.

ESI-MS: $M(C_{41}H_{70}N_2O_5Si_2)$=727.2, $(M+H)^+$=727.2.
Rf: Hexane/Acetone—50/50: 0.53.
$^1$H NMR (400 MHz, CDCl$_3$): δ=7.60 (s, 1H), 7.22 (m, 2H), 5.88 (m, 1H), 4.10 (m, 1H), 3.92 (m, 1H), 3.70 (s, 3H), 3.18 (m, 1H), 2.80 (m, 2H), 2.60 (s, 3H), 2.00 (m, 2H), 1.60 (m, 2H), 1.40 (m, 4H), 1.25 (s, 3H), 1.24 (d, 3H), 1.15 (s, 3H), 1.13 (d, 3H), 0.98 (s, 9H), 0.84 (s, 9H), 0.20 (m, 2H), 0.10 (s, 3H), 0.09 (s, 3H), 0.08 (s, 3H), −0.05 (s, 3H).

Example 17

Proliferation inhibition (IC50) of epothilone derivatives (Examples 1-16) towards KB-31 and KB-8511 cell lines. Method as described above.

|  | KB-31 [nmol l$^{-1}$] | KB-8511 [nmol l$^{-1}$] |
|---|---|---|
| Example 1 | 106.0 | 75.4 |
| Example 2 | 5.12 | 2.18 |
| Example 3 | 54.9 | 50.4 |
|  | 62.0 | 62.3 |
| Example 4 | 6.56 | 36.6 |
|  | 7.95 | 39.2 |
|  | 7.65 | 37.1 |
| Example 5 | 2.57 | 2.64 |
|  | 5.75 | 5.49 |
| Example 6 | <2 | <2 |
|  | 0.536 | 1.61 |
| Example 7 | 39.1 | 50.2 |
|  | 41.9 | 49.9 |
| Example 8 | 2.76 | 5.83 |

-continued

|  | KB-31 [nmol l⁻¹] | KB-8511 [nmol l⁻¹] |
|---|---|---|
| Example 9 | 3.91 | 10.3 |
|  | 4.79 | 13.3 |
|  | 2.07 | 4.37 |
|  | 3.7 | 10.5 |
| Example 10 | 0.588 | 6.89 |
|  | 0.594 | 6.15 |
|  | <2 | 3.25 |
|  | 0.596 | 6.83 |
| Example 11 | 2.57 | 25.1 |
|  | 5.17 | 36.6 |
|  | 4.63 | 37 |
| Example 12 | 0.27 | 1.45 |
|  | 0.24 | 1.67 |
|  | 0.228 | 0.96 |
| Example 13 | 144.2 | 74.1 |
|  | 137.7 | 68.8 |
|  | 152.5 | 73.5 |
| Example 14 | 5.0 | 12.4 |
|  | 3.5 | 9.92 |
| Example 15 | 0.467 | 1.01 |
| Example 16 | 0.149 | 0.11 |

What is claimed is:

1. A compound of formula I

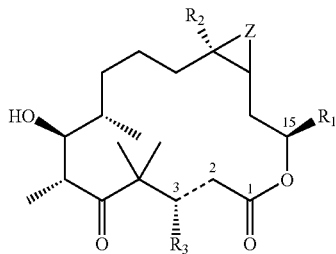

wherein
$R_1$ is

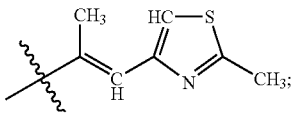

$R_2$ is lower alkyl or hydrogen;
$R_3$ is hydrogen;
Z is C; and
⁓ is a double bond between C2 and C3;
or salts thereof.

2. The compound of formula I according to claim 1, wherein
$R_1$ is

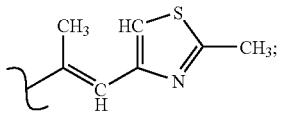

$R_2$ is lower alkyl; and
$R_3$ is hydrogen;
or salts thereof.

3. A pharmaceutical composition comprising the compound of formula I according to claim 1, or a salt thereof, provided that salt-forming groups are present, and one or more pharmaceutically acceptable carriers.

* * * * *